(12) United States Patent
Strachan et al.

(10) Patent No.: US 6,242,419 B1
(45) Date of Patent: Jun. 5, 2001

(54) COMPOSITIONS ISOLATED FROM STROMAL CELLS AND METHODS FOR THEIR USE

(75) Inventors: Lorna Strachan; Matthew Sleeman; Nevin Abernethy; Rene Onrust; Anand Kumble; Greg Murison, all of Auckland (NZ)

(73) Assignee: Genesis Research & Development Corporation Ltd., Parnell (NZ)

( * ) Notice: Subject to any disclaimer, the term of this patent is extended or adjusted under 35 U.S.C. 154(b) by 0 days.

(21) Appl. No.: 09/383,586

(22) Filed: Aug. 26, 1999

Related U.S. Application Data

(63) Continuation-in-part of application No. 09/276,268, filed on Mar. 25, 1999, now abandoned.

(51) Int. Cl.[7] .......................... A01N 37/18; A61K 38/16; A61K 38/00
(52) U.S. Cl. .................... 514/12; 514/2; 514/8; 530/380
(58) Field of Search ...................... 514/2, 8, 12; 530/380

(56) References Cited

FOREIGN PATENT DOCUMENTS 9963088    12/1999   (WO) .
0024756     5/2000   (WO) .

OTHER PUBLICATIONS

GenPept Assession No. CAB90552.
GenPept Assession No. AAC78827.
GenPept Assession No. AAC64321.
GenPept Assession No. AAD09175.
GenPept Assession No. AAB30638.
GenPept Assession No. CAA53271.
GenPept Assession No. CAA41209.
GenPept Assession No. AAB25535.
GenPept Assession No. CAB65272.
GenPept Assession No. AAF03400.
GenPept Assession No. AAF20364.
GenPept Assession No. BAA91786.
GenPept Assession No. AAB42225.
GenPept Assession No. AAC15584.
GenPept Assession No. AAF69825.
GenPept Assession No. BAA18909.
GenPept Assession No. AAC83205.
GenPept Assession No. CAB55955.
Swiss–Prot Assession No. P14730.
Swiss–Prot Assession No. P53104.
Swiss–Prot Assession No. Q14956.
Swiss–Prot Assession No. Q99969.
PIR Assession No. T17265.
PIR Assession No. S38579.
Gruss, Hans–Jürgen and Dower, Stephen K., "Tumor Necrosis Factor Ligand Superfamily: Involvement in the Pathology of Malignant Lymphomas", *Blood*, vol. 85, No. 12, pp. 3378–3404 (Jun. 15, 1995).
Banner, David W., et al., "Crystal Sructure of the Soluble Human 55 kd TNF Receptor–Human TNFβ Complex: Implications for TNF Receptor Activation", *Cell*, vol. 73, pp. 431–445 (May 7, 1993).
Maher, Pamela "p[38] Mitogen–activated Protein Kinase Activation Is Required for Fibroblast Growth Factor–2–stimulated Cell Proliferation but Not Differentiation", *The Journal of Biological Chemistry*, vol. 274, No. 25, pp. 17491–17498 (Jun. 18, 199).

*Primary Examiner*—David Saunders
*Assistant Examiner*—Amy DeCloux
(74) *Attorney, Agent, or Firm*—Janet Sleath; Ann W. Speckman

(57) ABSTRACT

Isolated polynucleotides encoding polypeptides expressed in mammalian fsn -/- lymph node stromal cells are provided, together with expression vectors and host cells comprising such isolated polynucleotides. In certain embodiments such polynucleotides encode members of the fibroblast growth factor receptor family. Methods for the use of such polynucleotides and polypeptides are also provided.

7 Claims, No Drawings

SEQUENCE LISTING

<160> NUMBER OF SEQ ID NOS: 38

<210> SEQ ID NO: 1
<211> LENGTH: 803
<212> TYPE: DNA
<213> ORGANISM: Mouse

<400> SEQUENCE: 1

| | | | | | |
|---|---|---|---|---|---|
| gttctgaatg | ggagcatcag | ccctctctgg | gctgttgccc | cgacattaca | ggtcctgtct | 60 |
| ctcagggacg | tgggccttgg | ttctggcgct | gcagagatgg | acttctctgc | gtttgggaat | 120 |
| ctgcgggcgt | tggatctgtc | gggaaactcc | ctgaccagct | tccaaaagtt | caagggcagt | 180 |
| ttggcccttc | ggactctcga | cctccgcaga | aactctctca | cggccctccc | tcagagggtt | 240 |
| gtgtccgagc | agcctctgag | gggtctgcag | accatctacc | tcagccagaa | cccttatgac | 300 |
| tgctgtgggg | tggaaggatg | gggggccctg | cagcagcact | caagactgt | tgcggacttg | 360 |
| tccatggtca | cttgcaacct | ctcttccaag | atcgtccgtg | tggtggagct | gcccgaaggc | 420 |
| ctgcctcagg | gctgtaagtg | ggaacaggtg | gacactggtc | tcttctacct | cgtgctcatc | 480 |
| ctgcccagct | gcctcaccct | gctggtggcc | tgtactgtcg | tcttcctcac | ttttaagaag | 540 |
| cctttgcttc | aggtcatcaa | gagccgctgc | cactggtcct | ccatatactg | acccgtgtgc | 600 |
| caaggctaga | gacttggttt | ttcctcgagg | atgcgtctct | ccgctggatc | tttacttttg | 660 |
| cagggtcga | gtgtgatgca | ttgaaggtta | aaactgaaat | ttgaaagagt | tccatcctca | 720 |
| gtcccattaa | cttctcctcc | catccgtgtg | atttatcctc | attgtcctgg | tgaaatattt | 780 |
| attaaacgac | attctgtgag | att | | | 803 |

<210> SEQ ID NO: 2
<211> LENGTH: 689
<212> TYPE: DNA
<213> ORGANISM: Mouse
<220> FEATURE:
<221> NAME/KEY: CDS
<222> LOCATION: (35)...(556)

<400> SEQUENCE: 2

```
gtcgcctgag gtccccgccg acgacgcact cacc atg gcg cct gct aac ctt ggg      55
                                     Met Ala Pro Ala Asn Leu Gly
                                       1               5 ctg acg ccg cac tgg gtg atg ctc ctc ggt gcc gtg ctg ctg ttg ctt       103
Leu Thr Pro His Trp Val Met Leu Leu Gly Ala Val Leu Leu Leu Leu
         10                  15                  20 ctg tcc gga gcc tcc gcg cag gaa cct ccg aga gtg ggt tgc tct gag       151
Leu Ser Gly Ala Ser Ala Gln Glu Pro Pro Arg Val Gly Cys Ser Glu
 25                  30                  35 tac aca aac aga tcc tgt gaa gag tgc ctc agg aat gtc tcc tgt ctg       199
Tyr Thr Asn Arg Ser Cys Glu Glu Cys Leu Arg Asn Val Ser Cys Leu
 40                  45                  50                  55 tgg tgc aat gag aac aag gcg tgt atg gac tac cca gtg agg aaa atc       247
Trp Cys Asn Glu Asn Lys Ala Cys Met Asp Tyr Pro Val Arg Lys Ile
                 60                  65                  70 ttg ccc cct gct tct ctc tgt aaa ttg agt tcc gct cgc tgg ggc gta       295
Leu Pro Pro Ala Ser Leu Cys Lys Leu Ser Ser Ala Arg Trp Gly Val
         75                  80                  85 tgc tgg gtg aac ttc gag gcc ttg atc atc acc atg tcg gtc ctg ggg       343
Cys Trp Val Asn Phe Glu Ala Leu Ile Ile Thr Met Ser Val Leu Gly
 90                  95                 100
```

```
ggc tct gtg ctc ctg ggc atc act gtg tgc tgc tgc tac tgc tgc cgc    391
Gly Ser Val Leu Leu Gly Ile Thr Val Cys Cys Cys Tyr Cys Cys Arg
    105                 110                 115 cgg aag aag agc cgg aag cca gac aag agc gat gag cgg gcc atg aga    439
Arg Lys Lys Ser Arg Lys Pro Asp Lys Ser Asp Glu Arg Ala Met Arg
120                 125                 130                 135 gag cag gag gag agg aga gtg cgg cag gag gaa agg agg gcg gaa atg    487
Glu Gln Glu Glu Arg Arg Val Arg Gln Glu Glu Arg Arg Ala Glu Met
                140                 145                 150 aag tca aga cat gat gaa atc agg aaa aaa tac ggt ctg ttt aaa gaa    535
Lys Ser Arg His Asp Glu Ile Arg Lys Lys Tyr Gly Leu Phe Lys Glu
                    155                 160                 165 caa aac ccg tat gag aag ttc taaggtggct ggcacacact tgtggtggat        586
Gln Asn Pro Tyr Glu Lys Phe
            170 cgtgcagttc cagagtttcc tgggaatgca ctccccagca gagcctgcag agacctcacc    646 accatggcca cccttgacct gggtgatccc tcagcctcta ctg                      689

<210> SEQ ID NO: 3
<211> LENGTH: 619
<212> TYPE: DNA
<213> ORGANISM: Mouse

<400> SEQUENCE: 3
ggcaccaggg aagccctgcc gcggcctgtc ccacagaacc tgcatcctca gatgccgccc     60
tatgcctttg ttcacccacc cttccccctg ccacctgtgc ggcccgtgtt caacaacttc    120
cccatcaaca tgggtcctgt gcccgctccc tatgtccccc ctctgcccaa cgtgcgtgtc    180
aactatgact ttggccacat gcacgtgccc ctggagcaca acctgccat gcactttggc     240 ccccaaccac ggcatcgctt ctgacaccca agccctgtc agccgtgccg agtctgtagg    300
agggcccagt ctcatcttct gagtaggggt gaaggcctcc attccctctc gaaagtggac    360
gcgtgtcctc ctgctcttac ctttgcaagg tccatgctcc ttcaggtctg atgccctctg    420
ggtgctgatt gtcactgggc aattataggg cagctccct agtctgccat cttagcagcc    480
aatccagtgg ccctgaccat gaagcaaggc ctctaatcgt ttgccatact tcctccccag    540
cagcccaatg aaagcccagg gggaaatggc taccatccc taagccaggg ctctctcctt    600
gttgcccaag gcccactta                                                 619

<210> SEQ ID NO: 4
<211> LENGTH: 1630
<212> TYPE: DNA
<213> ORGANISM: Mouse
<220> FEATURE:
<221> NAME/KEY: CDS
<222> LOCATION: (46)...(849)
<221> NAME/KEY: sig_peptide
<222> LOCATION: (46)...(150)

<400> SEQUENCE: 4
ggcgcgtgag cctcaggatg aaccctgtgt ttcctagcgg gctgt atg gct ctc ggt    57
                                                Met Ala Leu Gly
                                                        -35 ttt tct caa cgc tcc cgt atg gtg gcc gcg ggt gcc ggg gtg acc cgg    105
Phe Ser Gln Arg Ser Arg Met Val Ala Ala Gly Ala Gly Val Thr Arg
        -30                 -25                 -20 ctg cta gtg ctc ttg ctg atg gta gcc gcg gct cct agc aga gcc cga    153
Leu Leu Val Leu Leu Leu Met Val Ala Ala Ala Pro Ser Arg Ala Arg
-15                 -10                 -5                  1
```

-continued

```
ggc agc ggc tgc cgg gtc ggg gcc tcc gcg cgt ggg acc ggg gcc gat    201
Gly Ser Gly Cys Arg Val Gly Ala Ser Ala Arg Gly Thr Gly Ala Asp
          5                  10                  15 ggc cgt gaa gct gag ggc tgt ggc acc gtg gct ttg ctg ctg gag cat    249
Gly Arg Glu Ala Glu Gly Cys Gly Thr Val Ala Leu Leu Leu Glu His
         20                  25                  30 tca ttt gag ctc ggt gat gga gcc aac ttc cag aag cga ggc ttg ctg    297
Ser Phe Glu Leu Gly Asp Gly Ala Asn Phe Gln Lys Arg Gly Leu Leu
 35                  40                  45 ctc tgg aac cag cag gat ggc acc ctg tcg gca aca cag cga cag ctc    345
Leu Trp Asn Gln Gln Asp Gly Thr Leu Ser Ala Thr Gln Arg Gln Leu
 50                  55                  60                  65 agt gag gag gag cgt ggc cga ctc cgg gat gtg gct gct gtc aat ggc    393
Ser Glu Glu Glu Arg Gly Arg Leu Arg Asp Val Ala Ala Val Asn Gly
                 70                  75                  80 ctc tac agg gtc cgg gtc ccg agg cgg cct ggg aca ctt gat ggt tca    441
Leu Tyr Arg Val Arg Val Pro Arg Arg Pro Gly Thr Leu Asp Gly Ser
                 85                  90                  95 gaa gct ggc ggc cat gtg tct tcc ttc gtc cca gcg tgc tcc ctg gtg    489
Glu Ala Gly Gly His Val Ser Ser Phe Val Pro Ala Cys Ser Leu Val
            100                 105                 110 gag tcg cac ctt tcg gac cag ctg acc ttg cac gtg gat gtg gct ggc    537
Glu Ser His Leu Ser Asp Gln Leu Thr Leu His Val Asp Val Ala Gly
        115                 120                 125 aac gtg gtg ggc ctg tct gtg gtg gtg tac cct ggg ggc tgc cgg ggc    585
Asn Val Val Gly Leu Ser Val Val Val Tyr Pro Gly Gly Cys Arg Gly
130                 135                 140                 145 tcc gag gtg gaa gat gag gac ctg gag ctg ttc aat aca tct gtg cag    633
Ser Glu Val Glu Asp Glu Asp Leu Glu Leu Phe Asn Thr Ser Val Gln
                150                 155                 160 ctg cgg cct ccc agc act gct cca ggc ccc gag act gca gcc ttc att    681
Leu Arg Pro Pro Ser Thr Ala Pro Gly Pro Glu Thr Ala Ala Phe Ile
            165                 170                 175 gag cgc ctg gag atg gag cag gcc cag aag gcc aag aac cca cag gag    729
Glu Arg Leu Glu Met Glu Gln Ala Gln Lys Ala Lys Asn Pro Gln Glu
        180                 185                 190 cag aag tct ttc ttt gcc aaa tac tgg atg tac atc att cca gtt gtg    777
Gln Lys Ser Phe Phe Ala Lys Tyr Trp Met Tyr Ile Ile Pro Val Val
195                 200                 205 ctg ttc ctc atg atg tcg gga gcg ccg gac gct ggg ggc cag ggc ggc    825
Leu Phe Leu Met Met Ser Gly Ala Pro Asp Ala Gly Gly Gln Gly Gly
210                 215                 220                 225 ggt ggg ggc ggg ggc agc agc cgg tgagcagctg tgccacctag agcccccccc    879
Gly Gly Gly Gly Gly Ser Ser Arg
            230 agagccagcc caagaaggag ttcctgaccc cacatttccc tattgcatga atatggaagg    939 ctgtcccttc agtgagccct ctggccttcc tgtaagcccc tctttctgtc cctgagcctc    999 tctctcatcc tgttgactga gagcttgggt ggacctccct gtagccagct cactgcaact   1059 gtgtcccacc atgtggcact gtgctcctct gtctgctaaa cacccaccag cctgccccac   1119 cccacccccac catacacttt gggaacttgc caagctctct ccagcctctg tgcctttgcc   1179 ctgcaggccc cgtgcgcccc tcactgtcac tctccagccc tttgccaagg atctgtggcc   1239 cagaggcctc tgctcttagt ggctaggtca gcctccagcc cactgtccag gtggcatgct   1299 gtcttctttg ccccctctc tggtgcccca gaataccatg gtgacctacc actatccttt   1359 ctgcctttgg atgtcatagc ctggatcgtgt caccaggaga ggattgtggg cctccacgtt   1419 agtctgtgaa tgcacacttc gagtgacttg tgtgcaggtt ttgagagccg gttttgcact   1479
```

-continued

```
agctgctcga cagctgctgg catggccgtg ctcttgcaca tgcgccgctg tgggcatggg    1539
gattgctgtg cagcctcagc tgtgttgtgt ggctgctgat taaactgtcc cctaaacagc    1599
aaaaaaaaaa aaaaaaaaaa aaaaaaaaaa a                                   1630
```

<210> SEQ ID NO: 5
<211> LENGTH: 1197
<212> TYPE: DNA
<213> ORGANISM: Mouse
<220> FEATURE:
<221> NAME/KEY: CDS
<222> LOCATION: (346)...(543)
<221> NAME/KEY: sig_peptide
<222> LOCATION: (346)...(420)

<400> SEQUENCE: 5

```
ggcaccagac gactggggcc ctaccccatg tggacaacct caccatgcgt ctggaccccg     60
gtgtgggcgc ctcagtgata ggcgtagtga cagtgacagt gacagctaga gggatgatag    120 accccccaaac tagtggactt tgaagttttc ttcccagccg gttccagcct cctggaacaa   180
ccatgtcgcc agttttgcgc gtgccaaatt cacggcgctg cccaagcgga gctgctatct    240
gaattctcct tggatgtggc aaagggaaat gaacgcaaaa ggtgccgctg aagtgtccg     300 acctagagaa atatgtagac cggagccctg ttaccttcct ccagc atg gac ttc ctg    357
                                                Met Asp Phe Leu
                                                    -25 gtt ctc ttc ttg ttc tac ttg gcc ttc tta ttg att tgt gtt gtc ctg      405
Val Leu Phe Leu Phe Tyr Leu Ala Phe Leu Leu Ile Cys Val Val Leu
    -20              -15                 -10 atc tgc atc ttc aca aaa agc cag cgt ttg aag gcc gtg gtc ctt gga      453
Ile Cys Ile Phe Thr Lys Ser Gln Arg Leu Lys Ala Val Val Leu Gly
 -5               1               5                  10 gga gca cag gta gca ctg gtc ctt ggg tac tgc ccg gat gtg aat act      501
Gly Ala Gln Val Ala Leu Val Leu Gly Tyr Cys Pro Asp Val Asn Thr
            15              20                  25 gtg tta ggt gct agt ctg gaa ggc tca caa gac aag ggg atg              543
Val Leu Gly Ala Ser Leu Glu Gly Ser Gln Asp Lys Gly Met
        30              35              40 tgagtcttgt ctttaatcct ggcacttggg aggctgaggc ttcggggcca gttgggcta     603 catcgcaaga gcctgtgtcc aaacaaacaa acgttgtct ttttgctttg agataggtcg     663
aataggtcga attttcaagg ttggcttttt aaacagtgtg taatgtctgt atttggttgt    723
gactcctgtt tgcctagaca tgcttgtagc aggtgtgaac tcaggaggac acaagtgacc    783
agaaagctga gcatctagct gtcaatcttc ccttcacatt gtcccatctg tcttcccttg    843
ggggtcaaag caaagtgggg gcaagtagcc acgaaggggt tgacttggga ggaccctggg    903
gatctggagg ccaatcttga gcatggagca gacctgaggg ttagggaagc ccacgtccac    963
agcagcctct gcacaccccc ttccccaca gactccaaca gacacattct gtgcagtcaa    1023
ggtagaaatg gaggtgttct ctacacctcc taaatcctag cacttaggaa gctgaggcag   1083
gattatgaat tccaggctag ctcgggttat gtaatgagac tgtttcaaac acagagcgga   1143
gccgaggaga tggctgggca gtcacagagc tgccgtgcaa ccagaactgg aggg         1197
```

<210> SEQ ID NO: 6
<211> LENGTH: 1435
<212> TYPE: DNA
<213> ORGANISM: Mouse
<220> FEATURE:
<221> NAME/KEY: CDS
<222> LOCATION: (2)...(1015)

<221> NAME/KEY: sig_peptide
<222> LOCATION: (2)...(46)

<400> SEQUENCE: 6

| | | |
|---|---|---|
| c atg ggc gcc gtc tgg tca gcc ctg ctg gtc ggc ggg ggt cta gct gga<br>   Met Gly Ala Val Trp Ser Ala Leu Leu Val Gly Gly Gly Leu Ala Gly<br>   -15                 -10                       -5                              1 | 49 | |
| gcg ctc atc ctg tgg ctg ctg cgg gga gac tct ggg gcc ccg ggg aaa<br>Ala Leu Ile Leu Trp Leu Leu Arg Gly Asp Ser Gly Ala Pro Gly Lys<br>              5                        10                        15 | 97 | |
| gac ggg gtt gcg gag ccg ccg cag aag ggc gca cct cct ggg gag gct<br>Asp Gly Val Ala Glu Pro Pro Gln Lys Gly Ala Pro Pro Gly Glu Ala<br>        20                       25                      30 | 145 | |
| gcg gcc ccg gga gac ggt ccg ggt ggt ggt ggc agt ggc ggc ctg agc<br>Ala Ala Pro Gly Asp Gly Pro Gly Gly Gly Gly Ser Gly Gly Leu Ser<br>    35                        40                      45 | 193 | |
| cct gaa cct tcc gat cgg gag ctg gtc tcc aaa gca gag cat ctt cga<br>Pro Glu Pro Ser Asp Arg Glu Leu Val Ser Lys Ala Glu His Leu Arg<br>50                   55                        60                      65 | 241 | |
| gaa agc aac gga cat ttg att tct gag agc aaa gat ctt ggt aac ctg<br>Glu Ser Asn Gly His Leu Ile Ser Glu Ser Lys Asp Leu Gly Asn Leu<br>                 70                       75                      80 | 289 | |
| ccg gaa gca cag cgg ctg cag aat gtt gga gca gac tgg gtc aat gcc<br>Pro Glu Ala Gln Arg Leu Gln Asn Val Gly Ala Asp Trp Val Asn Ala<br>                85                       90                      95 | 337 | |
| aga gag ttt gtt cct gtt ggg aag att cca gac aca cac tcc agg gcc<br>Arg Glu Phe Val Pro Val Gly Lys Ile Pro Asp Thr His Ser Arg Ala<br>            100                     105                   110 | 385 | |
| gac tct gaa gcg gca aga aat caa agc cca gga tct cat gga gga gaa<br>Asp Ser Glu Ala Ala Arg Asn Gln Ser Pro Gly Ser His Gly Gly Glu<br>     115                   120                   125 | 433 | |
| tgg aga ctc ccc aaa gga caa gaa aca gct gtc aaa gta gct ggc agt<br>Trp Arg Leu Pro Lys Gly Gln Glu Thr Ala Val Lys Val Ala Gly Ser<br>130                 135                     140                   145 | 481 | |
| gtg gcc gca aag ctg gcc tcc agc agc ctg ctt gtg gac aga gct aaa<br>Val Ala Ala Lys Leu Ala Ser Ser Ser Leu Leu Val Asp Arg Ala Lys<br>               150                     155                   160 | 529 | |
| gca gtc agt cag gac cag gca ggc cac gag gac tgg gaa gtg gtg tct<br>Ala Val Ser Gln Asp Gln Ala Gly His Glu Asp Trp Glu Val Val Ser<br>            165                     170                   175 | 577 | |
| agg cac tca tct tgg ggg agt gtt ggt ttg ggt ggc agt ctt gag gct<br>Arg His Ser Ser Trp Gly Ser Val Gly Leu Gly Gly Ser Leu Glu Ala<br>               180                     185                   190 | 625 | |
| tct agg tta agt cta aat cag aga atg gac gac agc aca aac agt ctt<br>Ser Arg Leu Ser Leu Asn Gln Arg Met Asp Asp Ser Thr Asn Ser Leu<br>195                 200                     205 | 673 | |
| gtg gga gga aga ggc tgg gaa gta gat ggg aaa gtg gca tct ctg aaa<br>Val Gly Gly Arg Gly Trp Glu Val Asp Gly Lys Val Ala Ser Leu Lys<br>210                 215                     220                   225 | 721 | |
| cct caa cag gtc agc atc cag ttc cag gtg cac tac acc aca aac acc<br>Pro Gln Gln Val Ser Ile Gln Phe Gln Val His Tyr Thr Thr Asn Thr<br>            230                     235                   240 | 769 | |
| gat gtg cag ttc att gca gtg act gga gac cat gag agc ctt ggg aga<br>Asp Val Gln Phe Ile Ala Val Thr Gly Asp His Glu Ser Leu Gly Arg<br>            245                     250                   255 | 817 | |
| tgg aac aca tac atc cca ctc cac tac tgc aaa gac ggg ctc tgg tct<br>Trp Asn Thr Tyr Ile Pro Leu His Tyr Cys Lys Asp Gly Leu Trp Ser<br>            260                     265                   270 | 865 | |

-continued

```
cat tct gtc ttc ctg cct gca gac aca gtg gtg gag tgg aag ttc gtg    913
His Ser Val Phe Leu Pro Ala Asp Thr Val Val Glu Trp Lys Phe Val
    275                 280                 285 ttg gta gag aat aag gaa gtt act cgt tgg gaa gaa tgc agc aat aga    961
Leu Val Glu Asn Lys Glu Val Thr Arg Trp Glu Glu Cys Ser Asn Arg
290                 295                 300                 305 ttc ctg cag act ggc cat gag gat aaa gtg gtt cat ggg tgg tgg ggg   1009
Phe Leu Gln Thr Gly His Glu Asp Lys Val Val His Gly Trp Trp Gly
                310                 315                 320 att cac tgactcagtt ttcagagcat ccaagaggct gcagcagaat gtggacaagg    1065
Ile His ctaaggcttt agagcgcact gcatagctta agtaaaggc ggtgtgattc caattgtagc    1125
catcagggct ctttcagatt tgctagtgtg cttttgtcc aaaatgtagg aagatgtatg    1185
cctgcagata atgcttcctg taanctggca cttgtccctt attgtattga ctggtttgtg    1245
ctgacacatc aggacttgag gaattgatca tcctgggtag ttgcatcttg ggtagtacac    1305
ctgaggtatg gactacatat gggcaaggag caactaagca actgcacggg tacaaggtag    1365 agcgcctta gcagctctta gactagaaag actacaataa gccccatcaa acacagctaa    1425
agcaacactg                                                         1435
```

<210> SEQ ID NO: 7
<211> LENGTH: 1131
<212> TYPE: DNA
<213> ORGANISM: Mouse

<400> SEQUENCE: 7

```
ggcaccagcc cggcttctgt gctccgctca gtctccagcg atccctccct acctccgccc     60
tccatggcgt cgctcctgtg ctgtgggcct aagctggccg cctgtggcat cgtcctcagc    120
gcctggggag tgatcatgtt gataatgctc gggatatttt tcaatgtcca ttctgctgtg    180
ttaattgagg acgttccctt cacagagaaa gattttgaga acgtcctca gaacatatac     240 aacctgtacg agcaagtcag ctacaactgt tcatcgccg cgggcctcta cctcctcctc    300
ggaggcttct ccttctgcca agttcgtctc aacaagcgca aggaatacat ggtgcgctag    360
agcgcggtcc gcctctccct ccccagcccc cttctctatt taaagactcc gcagactccg    420
tcccactcat ctggcgtcct ttgggacttg tgaccctagc gagacgtcat ccctggccct    480
gcaaaactgc gcccagcctc tggaggagac cgagggtgac cgcgcccgt tctgaactac     540 aataaaaaga agcggttccc cctaagcttg ctgtctgtgc tttcagggag ggcgggccc    600 gggctggaag gggctgagac cggcctcatc gaggagtccg gaccctccga cggaagtgga    660
atgaagctag ccggaagtga agcaacgtct tccacctcgt cttcctccgc gcggcgaggc    720
cccttgagtg actggggaga ggtcgggtct cggccaatca gctgcaggga gggcgggact    780
ttctgcgcga gagcccgagc ggccggctgc cgggctctcc gtggtttcca gctcgcgtgg    840
tggtggtggc ggcggagcgt ctccgtgagg aggtgcgcgg ggccatgacg tcagcgtcca    900
ccaaggttgg agagatcttc tccgcggccg gcgccgcctt cacgaagctc ggggagttga    960
cgatgcagct gcatccagtc tcggactctt ccctgccgg tgccaagtgg acggagacgg   1020
agatagagat gctgagggct gctgtgaagc gctttgggga cgatcttaat cacatcagct   1080
gtgtcatcaa ggaacggaca gtggctcaga taaagaccac tgtgaagcga a           1131
```

<210> SEQ ID NO: 8
<211> LENGTH: 1357
<212> TYPE: DNA

```
<213> ORGANISM: Mouse
<220> FEATURE:
<221> NAME/KEY: CDS
<222> LOCATION: (150)...(989)

<400> SEQUENCE: 8
```

| | | |
|---|---|---|
| gggagggcct ggaggccgag gcgggcaggc accagccaga gcagctggcg gcagacggca | 60 |
| ggcagacagt cagaccgtct agcgggcctg gcttgcctac ctggcagctg cacccggtcc | 120 |
| ttcacccaga gctggttcca tagctcaac atg gtc ccc tgg ttc ctc ctg tct | 173 |
|  Met Val Pro Trp Phe Leu Leu Ser |
|  1               5 |
| ctg ctg cta ctt gcg agg cct gtg cct ggg gtg gcc tac tct gtg tca | 221 |
| Leu Leu Leu Leu Ala Arg Pro Val Pro Gly Val Ala Tyr Ser Val Ser |
|  10              15              20 |
| ctc ccg gcc tcc ttc ctg gag gat gta gcc ggc agc ggg gaa gct gag | 269 |
| Leu Pro Ala Ser Phe Leu Glu Asp Val Ala Gly Ser Gly Glu Ala Glu |
| 25              30              35              40 |
| ggt tct tca gcc tct tcc ccg agc ctg ccg ccg cct ggg act cca gcc | 317 |
| Gly Ser Ser Ala Ser Ser Pro Ser Leu Pro Pro Pro Gly Thr Pro Ala |
|          45              50              55 |
| ttc agt ccc aca ccg gag aga ccc cag ccc aca gct ctg gac ggc ccc | 365 |
| Phe Ser Pro Thr Pro Glu Arg Pro Gln Pro Thr Ala Leu Asp Gly Pro |
|  60              65              70 |
| gtg cca ccc acc aac ctc ctg gaa ggg atc atg gat ttc ttc cgg cag | 413 |
| Val Pro Pro Thr Asn Leu Leu Glu Gly Ile Met Asp Phe Phe Arg Gln |
|      75              80              85 |
| tac gtg atg ctc atc gcg gtg gtg ggc tcg ctg acc ttc ctc atc atg | 461 |
| Tyr Val Met Leu Ile Ala Val Val Gly Ser Leu Thr Phe Leu Ile Met |
|  90              95              100 |
| ttc ata gtc tgc gcc gcc ctc atc acg cgc cag aag cac aag gcc aca | 509 |
| Phe Ile Val Cys Ala Ala Leu Ile Thr Arg Gln Lys His Lys Ala Thr |
| 105             110             115             120 |
| gcc tac tac cca tcc tcg ttc cct gaa aag aag tat gtg gac cag aga | 557 |
| Ala Tyr Tyr Pro Ser Ser Phe Pro Glu Lys Lys Tyr Val Asp Gln Arg |
|          125             130             135 |
| gac cgg gct ggg gga ccc cgt acc ttc agc gag gtc cct gac agg gca | 605 |
| Asp Arg Ala Gly Gly Pro Arg Thr Phe Ser Glu Val Pro Asp Arg Ala |
|      140             145             150 |
| cct gac agc cgg cat gaa gaa ggc ctg gac acc tcc cat cag ctc cag | 653 |
| Pro Asp Ser Arg His Glu Glu Gly Leu Asp Thr Ser His Gln Leu Gln |
|  155             160             165 |
| gct gac att ctg gct gct acc cag aac ctc cgg tct cca gct aga gcc | 701 |
| Ala Asp Ile Leu Ala Ala Thr Gln Asn Leu Arg Ser Pro Ala Arg Ala |
|     170             175             180 |
| ctg cca ggc aat ggg gag gga gca aag cct gtg aag ggt ggg tcg gag | 749 |
| Leu Pro Gly Asn Gly Glu Gly Ala Lys Pro Val Lys Gly Gly Ser Glu |
| 185             190             195             200 |
| gag gag gag gaa gag gtg ctc agc ggt cag gag gag gcc cag gaa gcc | 797 |
| Glu Glu Glu Glu Glu Val Leu Ser Gly Gln Glu Glu Ala Gln Glu Ala |
|          205             210             215 |
| cca gta tgt ggg gtc act gaa gag aag ctg ggg gtc cca gag gag tcg | 845 |
| Pro Val Cys Gly Val Thr Glu Glu Lys Leu Gly Val Pro Glu Glu Ser |
|      220             225             230 |
| gtc tca gca gag gct gaa ggg gtt cct gcc acc agt gag ggc caa ggg | 893 |
| Val Ser Ala Glu Ala Glu Gly Val Pro Ala Thr Ser Glu Gly Gln Gly |
|  235             240             245 |
| gaa gca gaa ggg tct ttc tcc tta gcc cag gaa tcc cag gga gca act | 941 |
| Glu Ala Glu Gly Ser Phe Ser Leu Ala Gln Glu Ser Gln Gly Ala Thr |
|     250             255             260 |

-continued

| | |
|---|---|
| ggt cct cct gaa agt ccc tgt gcc tgc aac aga gtc tcc ccc agt gtc<br>Gly Pro Pro Glu Ser Pro Cys Ala Cys Asn Arg Val Ser Pro Ser Val<br>265                       270                      275                      280 | 989 |
| taacaggccc cagaactgct gggacccgaa tgttgggtcc ttgagggtca cctctttggt | 1049 |
| caagaaaggc attcagctct aactgctcct tgataccacg tggcttggcc attgctggtg | 1109 |
| ccaaggctga ccccgaactg gcagagccga tgccctctgg tgcacccag gaaacatctc | 1169 |
| cccaagttcc agcgccctta atgactcttg ccaccctggg ggcttcaccc taacgcacca | 1229 |
| cttctctgga aggggaaggc cagacacatg ccagttgggg ctgcatgagg cagtcctcag | 1289 |
| agcagaaggg gaccaggcca gaggccacct gtgacgggc aaactgcatc tcggctgtgg | 1349 |
| agaccaga | 1357 |

<210> SEQ ID NO: 9
<211> LENGTH: 815
<212> TYPE: DNA
<213> ORGANISM: Mouse
<220> FEATURE:
<221> NAME/KEY: CDS
<222> LOCATION: (119)...(682)
<221> NAME/KEY: sig_peptide
<222> LOCATION: (119)...(205)

<400> SEQUENCE: 9

| | |
|---|---|
| aggtcgacac tagtggatcc aaagaattcg gcacgagggg acgcggagcg gtcgcgtgcg | 60 |
| cggagagcag ctctgggcgc cgggcggttg ctgcgggcgc tcaggggccc tgggaaca | 118 |
| atg gcg ctg tgc gcg cgg gcc gcg ctg ctg ctg ggc gtg ctg cag gtg<br>Met Ala Leu Cys Ala Arg Ala Ala Leu Leu Leu Gly Val Leu Gln Val<br>                       -25                      -20                      -15 | 166 |
| ctg gcg ctg cta ggg gcg gcg cag gac ccg acc gac gct cag ggc tct<br>Leu Ala Leu Leu Gly Ala Ala Gln Asp Pro Thr Asp Ala Gln Gly Ser<br>             -10                      -5                        1 | 214 |
| gca agt gga aac cac tca gtg ctg acc tcc aat att aac ata aca gag<br>Ala Ser Gly Asn His Ser Val Leu Thr Ser Asn Ile Asn Ile Thr Glu<br>5                      10                          15 | 262 |
| aat acc aac cag acc atg agt gtg gtt tcc aac cag acc agt gaa atg<br>Asn Thr Asn Gln Thr Met Ser Val Val Ser Asn Gln Thr Ser Glu Met<br>20                        25                        30                      35 | 310 |
| cag agc acc gcg aag cct tcc gta ctg cca aaa act acc aca ctt atc<br>Gln Ser Thr Ala Lys Pro Ser Val Leu Pro Lys Thr Thr Thr Leu Ile<br>                40                        45                      50 | 358 |
| act gtg aaa cct gca act att gtt aaa ata tca acc cca gga gtc tta<br>Thr Val Lys Pro Ala Thr Ile Val Lys Ile Ser Thr Pro Gly Val Leu<br>                   55                        60                      65 | 406 |
| cca cat gtg acg cct act gcc tca aag tct aca ccc aat gca agt gct<br>Pro His Val Thr Pro Thr Ala Ser Lys Ser Thr Pro Asn Ala Ser Ala<br>                70                        75                        80 | 454 |
| tct cca aac tct acc cac acg tca gca tcc atg aca acc cca gcc cac<br>Ser Pro Asn Ser Thr His Thr Ser Ala Ser Met Thr Thr Pro Ala His<br>                85                        90                        95 | 502 |
| agt agt tta ttg aca act gta acg gtt tca gca act act cat ccc acc<br>Ser Ser Leu Leu Thr Thr Val Thr Val Ser Ala Thr Thr His Pro Thr<br>100                     105                    110                    115 | 550 |
| aaa ggc aaa gga tcc aag ttt gat gcc ggc agc ttt gtt ggt ggt ata<br>Lys Gly Lys Gly Ser Lys Phe Asp Ala Gly Ser Phe Val Gly Gly Ile<br>                   120                    125                    130 | 598 |
| ggt gtt aac act ggg agt ttt atc tat tct cta cat tgg atg caa aat<br>Gly Val Asn Thr Gly Ser Phe Ile Tyr Ser Leu His Trp Met Gln Asn<br>                 135                    140                    145 | 646 |

-continued

```
gta tta ttc aag aag agg cat tcg gta ccg aag cat tgacgaacat          692
Val Leu Phe Lys Lys Arg His Ser Val Pro Lys His
            150                 155 gatgccatca tttaaagtac ttcagtggtc aaggaaagaa gaaagactgc agccttatca   752
attattttgg tttatattag tttaaactat tattttcttg gaagtagtat aaacaagtca   812
tgc                                                                 815

<210> SEQ ID NO: 10
<211> LENGTH: 1129
<212> TYPE: DNA
<213> ORGANISM: Mouse
<220> FEATURE:
<221> NAME/KEY: CDS
<222> LOCATION: (13)...(963)
<221> NAME/KEY: sig_peptide
<222> LOCATION: (13)...(90)

<400> SEQUENCE: 10
ccaacactcg cc atg cgt tct ggg gca ctg tgg ccg ctg ctt tgg gga gcc   51
              Met Arg Ser Gly Ala Leu Trp Pro Leu Leu Trp Gly Ala
              -25                 -20                 -15 ctg gtc tgg aca gtg gga tcc gtg ggc gcc gtg atg ggc tcc gag gat    99
Leu Val Trp Thr Val Gly Ser Val Gly Ala Val Met Gly Ser Glu Asp
        -10                 -5                  1 tct gtg ccc ggt ggc gtg tgc tgg ctc cag cag ggc aga gag gcc acc   147
Ser Val Pro Gly Gly Val Cys Trp Leu Gln Gln Gly Arg Glu Ala Thr
  5                  10                  15 tgc agt ctg gtg ctg aag act cgt gtc agc cgg gag gag tgc tgt gct   195
Cys Ser Leu Val Leu Lys Thr Arg Val Ser Arg Glu Glu Cys Cys Ala
 20                  25                  30                  35 tcc ggc aac atc aac acc gcc tgg tcc aac ttc acc cac cca ggc aat   243
Ser Gly Asn Ile Asn Thr Ala Trp Ser Asn Phe Thr His Pro Gly Asn
                 40                  45                  50 aaa atc agc ctg cta ggg ttc ctg ggc ctc gtc cac tgc ctc ccc tgc   291
Lys Ile Ser Leu Leu Gly Phe Leu Gly Leu Val His Cys Leu Pro Cys
         55                  60                  65 aaa gat tcc tgc gac gga gtg gag tgc ggc ccc ggc aag gcg tgc cgc   339
Lys Asp Ser Cys Asp Gly Val Glu Cys Gly Pro Gly Lys Ala Cys Arg
     70                  75                  80 aat gct ggg ggg gcg tcc aac aac tgc gag tgc gtg ccc aac tgc gag   387
Asn Ala Gly Gly Ala Ser Asn Asn Cys Glu Cys Val Pro Asn Cys Glu
 85                  90                  95 ggg ttt ccc gcg ggc ttc cag gtc tgc ggc tct gat ggc gcc acc tac   435
Gly Phe Pro Ala Gly Phe Gln Val Cys Gly Ser Asp Gly Ala Thr Tyr
100                 105                 110                 115 cgg gac gaa tgc gaa ctg cgc acc gcg cgc tgt cgc gga cac cca gac   483
Arg Asp Glu Cys Glu Leu Arg Thr Ala Arg Cys Arg Gly His Pro Asp
                120                 125                 130 ttg cgc gtc atg tac cgc ggc cgc tgt caa aag tct tgc gct cag gta   531
Leu Arg Val Met Tyr Arg Gly Arg Cys Gln Lys Ser Cys Ala Gln Val
            135                 140                 145 gtg tgc ccg cgt ccc cag tcg tgc ctt gtg gat cag acc ggc agc gca   579
Val Cys Pro Arg Pro Gln Ser Cys Leu Val Asp Gln Thr Gly Ser Ala
        150                 155                 160 cac tgc gtg gtg tgt cgc gct gcg ccc tgc cca gta cct tcc aac ccc   627
His Cys Val Val Cys Arg Ala Ala Pro Cys Pro Val Pro Ser Asn Pro
    165                 170                 175 ggc caa gaa ctc tgt ggc aac aac aac gtt acc tac atc tcg tcg tgt   675
Gly Gln Glu Leu Cys Gly Asn Asn Asn Val Thr Tyr Ile Ser Ser Cys
180                 185                 190                 195
```

```
cac ctg cgc cag gcc act tgc ttc ctg ggc cgc tcc att ggg gtt cgg      723
His Leu Arg Gln Ala Thr Cys Phe Leu Gly Arg Ser Ile Gly Val Arg
            200                 205                 210 cac cca ggc atc tgc aca ggt ggc ccc aag ttc ctg aag tct ggc gat      771
His Pro Gly Ile Cys Thr Gly Gly Pro Lys Phe Leu Lys Ser Gly Asp
        215                 220                 225 gct gcc att gtt gat atg gtc cct ggc aag ccc atg tgt gtt gag agc      819
Ala Ala Ile Val Asp Met Val Pro Gly Lys Pro Met Cys Val Glu Ser
            230                 235                 240 ttc tct gac tac cct cca ctt ggt cgc ttt gct gtt cgt gac atg agg      867
Phe Ser Asp Tyr Pro Pro Leu Gly Arg Phe Ala Val Arg Asp Met Arg
        245                 250                 255 cag aca gtt gct gtg ggt gtc atc aaa gct gtg gac aag aag gct gct      915
Gln Thr Val Ala Val Gly Val Ile Lys Ala Val Asp Lys Lys Ala Ala
260                 265                 270                 275 gga gct ggc aaa gtc acc aag tct gcc cag aaa gct cag aag gct aaa      963
Gly Ala Gly Lys Val Thr Lys Ser Ala Gln Lys Ala Gln Lys Ala Lys
            280                 285                 290 tgaatattac ccctaacacc tgccacccca gtcttaatca gtggtggaag aacggtctca   1023
gaactgtttg tctcaattgg ccatttaagt ttaatagtaa aagactggtt aatgataaca   1083
atgcatcgta aaaccttcag aaggaaagaa tgttgtggac catttt                 1129

<210> SEQ ID NO: 11
<211> LENGTH: 196
<212> TYPE: PRT
<213> ORGANISM: Mouse

<400> SEQUENCE: 11

Val Leu Asn Gly Ser Ile Ser Pro Leu Trp Ala Val Ala Pro Thr Leu
1               5                   10                  15

Gln Val Leu Ser Leu Arg Asp Val Gly Leu Gly Ser Gly Ala Ala Glu
            20                  25                  30

Met Asp Phe Ser Ala Phe Gly Asn Leu Arg Ala Leu Asp Leu Ser Gly
        35                  40                  45

Asn Ser Leu Thr Ser Phe Gln Lys Phe Lys Gly Ser Leu Ala Leu Arg
    50                  55                  60

Thr Leu Asp Leu Arg Arg Asn Ser Leu Thr Ala Leu Pro Gln Arg Val
65                  70                  75                  80

Val Ser Glu Gln Pro Leu Arg Gly Leu Gln Thr Ile Tyr Leu Ser Gln
                85                  90                  95

Asn Pro Tyr Asp Cys Cys Gly Val Glu Gly Trp Gly Ala Leu Gln Gln
            100                 105                 110

His Phe Lys Thr Val Ala Asp Leu Ser Met Val Thr Cys Asn Leu Ser
        115                 120                 125

Ser Lys Ile Val Arg Val Val Glu Leu Pro Glu Gly Leu Pro Gln Gly
    130                 135                 140

Cys Lys Trp Glu Gln Val Asp Thr Gly Leu Phe Tyr Leu Val Leu Ile
145                 150                 155                 160

Leu Pro Ser Cys Leu Thr Leu Leu Val Ala Cys Thr Val Val Phe Leu
                165                 170                 175

Thr Phe Lys Lys Pro Leu Leu Gln Val Ile Lys Ser Arg Cys His Trp
            180                 185                 190

Ser Ser Ile Tyr
            195
```

```
<210> SEQ ID NO: 12
<211> LENGTH: 174
<212> TYPE: PRT
<213> ORGANISM: Mouse

<400> SEQUENCE: 12

Met Ala Pro Ala Asn Leu Gly Leu Thr Pro His Trp Val Met Leu Leu
1               5                   10                  15

Gly Ala Val Leu Leu Leu Leu Ser Gly Ala Ser Ala Gln Glu Pro
            20                  25                  30

Pro Arg Val Gly Cys Ser Glu Tyr Thr Asn Arg Ser Cys Glu Cys
            35                  40                  45

Leu Arg Asn Val Ser Cys Leu Trp Cys Asn Glu Asn Lys Ala Cys Met
    50                  55                  60

Asp Tyr Pro Val Arg Lys Ile Leu Pro Pro Ala Ser Leu Cys Lys Leu
65                  70                  75                  80

Ser Ser Ala Arg Trp Gly Val Cys Trp Val Asn Phe Glu Ala Leu Ile
                85                  90                  95

Ile Thr Met Ser Val Leu Gly Gly Ser Val Leu Leu Gly Ile Thr Val
                100                 105                 110

Cys Cys Cys Tyr Cys Cys Arg Arg Lys Lys Ser Arg Lys Pro Asp Lys
            115                 120                 125

Ser Asp Glu Arg Ala Met Arg Glu Gln Glu Gly Arg Arg Val Arg Gln
    130                 135                 140

Glu Glu Arg Arg Ala Glu Met Lys Ser Arg His Asp Glu Ile Arg Lys
145                 150                 155                 160

Lys Tyr Gly Leu Phe Lys Glu Gln Asn Pro Tyr Glu Lys Phe
                165                 170

<210> SEQ ID NO: 13
<211> LENGTH: 106
<212> TYPE: PRT
<213> ORGANISM: Mouse

<400> SEQUENCE: 13

Ala Pro Gly Lys Pro Cys Arg Gly Leu Ser His Arg Thr Cys Ile Leu
1               5                   10                  15

Arg Cys Arg Pro Met Pro Leu Phe Thr His Pro Ser Pro Cys His Leu
            20                  25                  30

Cys Gly Pro Cys Ser Thr Thr Ser Pro Ser Thr Trp Val Leu Cys Pro
            35                  40                  45

Leu Pro Met Ser Pro Leu Cys Pro Thr Cys Val Ser Thr Met Thr Leu
    50                  55                  60

Ala Thr Cys Thr Cys Pro Trp Ser Thr Thr Cys Pro Cys Thr Leu Ala
65                  70                  75                  80

Pro Asn His Gly Ile Ala Ser Asp Thr Gln Ser Pro Val Ser Arg Ala
                85                  90                  95

Glu Ser Val Gly Gly Pro Ser Leu Ile Phe
                100                 105

<210> SEQ ID NO: 14
<211> LENGTH: 268
<212> TYPE: PRT
<213> ORGANISM: Mouse

<400> SEQUENCE: 14

Met Ala Leu Gly Phe Ser Gln Arg Ser Arg Met Val Ala Ala Gly Ala
1               5                   10                  15
```

```
Gly Val Thr Arg Leu Leu Val Leu Leu Met Val Ala Ala Ala Pro
            20                  25                  30

Ser Arg Ala Arg Gly Ser Gly Cys Arg Val Gly Ala Ser Ala Arg Gly
            35                  40                  45

Thr Gly Ala Asp Gly Arg Glu Ala Glu Gly Cys Gly Thr Val Ala Leu
    50                  55                  60

Leu Leu Glu His Ser Phe Glu Leu Gly Asp Gly Ala Asn Phe Gln Lys
65                  70                  75                  80

Arg Gly Leu Leu Leu Trp Asn Gln Gln Asp Gly Thr Leu Ser Ala Thr
                85                  90                  95

Gln Arg Gln Leu Ser Glu Glu Arg Gly Arg Leu Arg Asp Val Ala
            100                 105                 110

Ala Val Asn Gly Leu Tyr Arg Val Arg Val Pro Arg Pro Gly Thr
            115                 120                 125

Leu Asp Gly Ser Glu Ala Gly Gly His Val Ser Ser Phe Val Pro Ala
    130                 135                 140

Cys Ser Leu Val Glu Ser His Leu Ser Asp Gln Leu Thr Leu His Val
145                 150                 155                 160

Asp Val Ala Gly Asn Val Val Gly Leu Ser Val Val Tyr Pro Gly
                165                 170                 175

Gly Cys Arg Gly Ser Glu Val Glu Asp Glu Asp Leu Glu Leu Phe Asn
            180                 185                 190

Thr Ser Val Gln Leu Arg Pro Pro Ser Thr Ala Pro Gly Pro Glu Thr
    195                 200                 205

Ala Ala Phe Ile Glu Arg Leu Glu Met Glu Gln Ala Gln Lys Ala Lys
    210                 215                 220

Asn Pro Gln Glu Gln Lys Ser Phe Phe Ala Lys Tyr Trp Met Tyr Ile
225                 230                 235                 240

Ile Pro Val Val Leu Phe Leu Met Met Ser Gly Ala Pro Asp Ala Gly
                245                 250                 255

Gly Gln Gly Gly Gly Gly Gly Gly Ser Ser Arg
            260                 265

<210> SEQ ID NO: 15
<211> LENGTH: 66
<212> TYPE: PRT
<213> ORGANISM: Mouse

<400> SEQUENCE: 15

Met Asp Phe Leu Val Leu Phe Leu Phe Tyr Leu Ala Phe Leu Leu Ile
1               5                   10                  15

Cys Val Val Leu Ile Cys Ile Phe Thr Lys Ser Gln Arg Leu Lys Ala
            20                  25                  30

Val Val Leu Gly Gly Ala Gln Val Ala Leu Val Leu Gly Tyr Cys Pro
            35                  40                  45

Asp Val Asn Thr Val Leu Gly Ala Ser Leu Glu Gly Ser Gln Asp Lys
    50                  55                  60

Gly Met
65

<210> SEQ ID NO: 16
<211> LENGTH: 338
<212> TYPE: PRT
<213> ORGANISM: Mouse
```

-continued

```
<400> SEQUENCE: 16

Met Gly Ala Val Trp Ser Ala Leu Leu Val Gly Gly Leu Ala Gly
 1               5                  10                  15

Ala Leu Ile Leu Trp Leu Leu Arg Gly Asp Ser Gly Ala Pro Gly Lys
            20                  25                  30

Asp Gly Val Ala Glu Pro Pro Gln Lys Gly Ala Pro Pro Gly Glu Ala
        35                  40                  45

Ala Ala Pro Gly Asp Gly Pro Gly Gly Gly Ser Gly Gly Leu Ser
50                  55                  60

Pro Glu Pro Ser Asp Arg Glu Leu Val Ser Lys Ala Glu His Leu Arg
65                  70                  75                  80

Glu Ser Asn Gly His Leu Ile Ser Glu Ser Lys Asp Leu Gly Asn Leu
                85                  90                  95

Pro Glu Ala Gln Arg Leu Gln Asn Val Gly Ala Asp Trp Val Asn Ala
            100                 105                 110

Arg Glu Phe Val Pro Val Gly Lys Ile Pro Asp Thr His Ser Arg Ala
        115                 120                 125

Asp Ser Glu Ala Ala Arg Asn Gln Ser Pro Gly Ser His Gly Gly Glu
    130                 135                 140

Trp Arg Leu Pro Lys Gly Gln Glu Thr Ala Val Lys Val Ala Gly Ser
145                 150                 155                 160

Val Ala Ala Lys Leu Ala Ser Ser Leu Leu Val Asp Arg Ala Lys
                165                 170                 175

Ala Val Ser Gln Asp Gln Ala Gly His Glu Asp Trp Glu Val Val Ser
            180                 185                 190

Arg His Ser Ser Trp Gly Ser Val Gly Leu Gly Gly Ser Leu Glu Ala
        195                 200                 205

Ser Arg Leu Ser Leu Asn Gln Arg Met Asp Asp Ser Thr Asn Ser Leu
    210                 215                 220

Val Gly Gly Arg Gly Trp Glu Val Asp Gly Lys Val Ala Ser Leu Lys
225                 230                 235                 240

Pro Gln Gln Val Ser Ile Gln Phe Gln Val His Tyr Thr Thr Asn Thr
                245                 250                 255

Asp Val Gln Phe Ile Ala Val Thr Gly Asp His Glu Ser Leu Gly Arg
            260                 265                 270

Trp Asn Thr Tyr Ile Pro Leu His Tyr Cys Lys Asp Gly Leu Trp Ser
        275                 280                 285

His Ser Val Phe Leu Pro Ala Asp Thr Val Val Glu Trp Lys Phe Val
    290                 295                 300

Leu Val Glu Asn Lys Glu Val Thr Arg Trp Glu Glu Cys Ser Asn Arg
305                 310                 315                 320

Phe Leu Gln Thr Gly His Glu Asp Lys Val Val His Gly Trp Trp Gly
                325                 330                 335

Ile His

<210> SEQ ID NO: 17
<211> LENGTH: 119
<212> TYPE: PRT
<213> ORGANISM: Mouse

<400> SEQUENCE: 17

Gly Thr Ser Pro Ala Ser Val Leu Arg Ser Val Ser Ser Asp Pro Ser
 1               5                  10                  15
```

-continued

Leu Pro Pro Pro Ser Met Ala Ser Leu Leu Cys Cys Gly Pro Lys Leu
            20                  25                  30

Ala Ala Cys Gly Ile Val Leu Ser Ala Trp Gly Val Ile Met Leu Ile
        35                  40                  45

Met Leu Gly Ile Phe Phe Asn Val His Ser Ala Val Leu Ile Glu Asp
    50                  55                  60

Val Pro Phe Thr Glu Lys Asp Phe Glu Asn Gly Pro Gln Asn Ile Tyr
65                  70                  75                  80

Asn Leu Tyr Glu Gln Val Ser Tyr Asn Cys Phe Ile Ala Ala Gly Leu
                85                  90                  95

Tyr Leu Leu Gly Gly Phe Ser Phe Cys Gln Val Arg Leu Asn Lys
                100                 105                 110

Arg Lys Glu Tyr Met Val Arg
            115

<210> SEQ ID NO: 18
<211> LENGTH: 280
<212> TYPE: PRT
<213> ORGANISM: Mouse

<400> SEQUENCE: 18

Met Val Pro Trp Phe Leu Leu Ser Leu Leu Leu Ala Arg Pro Val
1               5                   10                  15

Pro Gly Val Ala Tyr Ser Val Ser Leu Pro Ala Ser Phe Leu Glu Asp
            20                  25                  30

Val Ala Gly Ser Gly Glu Ala Glu Gly Ser Ser Ala Ser Ser Pro Ser
        35                  40                  45

Leu Pro Pro Gly Thr Pro Ala Phe Ser Pro Thr Pro Glu Arg Pro
    50                  55                  60

Gln Pro Thr Ala Leu Asp Gly Pro Val Pro Pro Thr Asn Leu Leu Glu
65                  70                  75                  80

Gly Ile Met Asp Phe Phe Arg Gln Tyr Val Met Leu Ile Ala Val Val
                85                  90                  95

Gly Ser Leu Thr Phe Leu Ile Met Phe Ile Val Cys Ala Ala Leu Ile
                100                 105                 110

Thr Arg Gln Lys His Lys Ala Thr Ala Tyr Tyr Pro Ser Ser Phe Pro
            115                 120                 125

Glu Lys Lys Tyr Val Asp Gln Arg Asp Arg Ala Gly Gly Pro Arg Thr
    130                 135                 140

Phe Ser Glu Val Pro Asp Arg Ala Pro Asp Ser Arg His Glu Glu Gly
145                 150                 155                 160

Leu Asp Thr Ser His Gln Leu Gln Ala Asp Ile Leu Ala Ala Thr Gln
                165                 170                 175

Asn Leu Arg Ser Pro Ala Arg Ala Leu Pro Gly Asn Gly Glu Gly Ala
            180                 185                 190

Lys Pro Val Lys Gly Gly Ser Glu Glu Glu Glu Glu Val Leu Ser
    195                 200                 205

Gly Gln Glu Glu Ala Gln Glu Ala Pro Val Cys Gly Val Thr Glu Glu
    210                 215                 220

Lys Leu Gly Val Pro Glu Glu Ser Val Ser Ala Glu Ala Glu Gly Val
225                 230                 235                 240

Pro Ala Thr Ser Glu Gly Gln Gly Glu Ala Glu Gly Ser Phe Ser Leu
                245                 250                 255

```
Ala Gln Glu Ser Gln Gly Ala Thr Gly Pro Pro Glu Ser Pro Cys Ala
            260                 265                 270

Cys Asn Arg Val Ser Pro Ser Val
            275                 280

<210> SEQ ID NO: 19
<211> LENGTH: 188
<212> TYPE: PRT
<213> ORGANISM: Mouse

<400> SEQUENCE: 19

Met Ala Leu Cys Ala Arg Ala Ala Leu Leu Leu Gly Val Leu Gln Val
  1               5                  10                  15

Leu Ala Leu Leu Gly Ala Ala Gln Asp Pro Thr Asp Ala Gln Gly Ser
                 20                  25                  30

Ala Ser Gly Asn His Ser Val Leu Thr Ser Asn Ile Asn Ile Thr Glu
             35                  40                  45

Asn Thr Asn Gln Thr Met Ser Val Val Ser Asn Gln Thr Ser Glu Met
 50                  55                  60

Gln Ser Thr Ala Lys Pro Ser Val Leu Pro Lys Thr Thr Thr Leu Ile
 65                  70                  75                  80

Thr Val Lys Pro Ala Thr Ile Val Lys Ile Ser Thr Pro Gly Val Leu
                 85                  90                  95

Pro His Val Thr Pro Thr Ala Ser Lys Ser Thr Pro Asn Ala Ser Ala
                100                 105                 110

Ser Pro Asn Ser Thr His Thr Ser Ala Ser Met Thr Thr Pro Ala His
            115                 120                 125

Ser Ser Leu Leu Thr Thr Val Thr Val Ser Ala Thr Thr His Pro Thr
        130                 135                 140

Lys Gly Lys Gly Ser Lys Phe Asp Ala Gly Ser Phe Val Gly Gly Ile
145                 150                 155                 160

Gly Val Asn Thr Gly Ser Phe Ile Tyr Ser Leu His Trp Met Gln Asn
                165                 170                 175

Val Leu Phe Lys Lys Arg His Ser Val Pro Lys His
            180                 185

<210> SEQ ID NO: 20
<211> LENGTH: 317
<212> TYPE: PRT
<213> ORGANISM: Mouse

<400> SEQUENCE: 20

Met Arg Ser Gly Ala Leu Trp Pro Leu Leu Trp Gly Ala Leu Val Trp
  1               5                  10                  15

Thr Val Gly Ser Val Gly Ala Val Met Gly Ser Glu Asp Ser Val Pro
                 20                  25                  30

Gly Gly Val Cys Trp Leu Gln Gln Gly Arg Glu Ala Thr Cys Ser Leu
             35                  40                  45

Val Leu Lys Thr Arg Val Ser Arg Glu Glu Cys Cys Ala Ser Gly Asn
 50                  55                  60

Ile Asn Thr Ala Trp Ser Asn Phe Thr His Pro Gly Asn Lys Ile Ser
 65                  70                  75                  80

Leu Leu Gly Phe Leu Gly Leu Val His Cys Leu Pro Cys Lys Asp Ser
                 85                  90                  95

Cys Asp Gly Val Glu Cys Gly Pro Gly Lys Ala Cys Arg Asn Ala Gly
                100                 105                 110
```

-continued

```
Gly Ala Ser Asn Asn Cys Glu Cys Val Pro Asn Cys Glu Gly Phe Pro
        115                 120                 125
Ala Gly Phe Gln Val Cys Gly Ser Asp Gly Ala Thr Tyr Arg Asp Glu
    130                 135                 140
Cys Glu Leu Arg Thr Ala Arg Cys Arg Gly His Pro Asp Leu Arg Val
145                 150                 155                 160
Met Tyr Arg Gly Arg Cys Gln Lys Ser Cys Ala Gln Val Val Cys Pro
                165                 170                 175
Arg Pro Gln Ser Cys Leu Val Asp Gln Thr Gly Ser Ala His Cys Val
            180                 185                 190
Val Cys Arg Ala Ala Pro Cys Pro Val Pro Ser Asn Pro Gly Gln Glu
        195                 200                 205
Leu Cys Gly Asn Asn Asn Val Thr Tyr Ile Ser Ser Cys His Leu Arg
    210                 215                 220
Gln Ala Thr Cys Phe Leu Gly Arg Ser Ile Gly Val Arg His Pro Gly
225                 230                 235                 240
Ile Cys Thr Gly Gly Pro Lys Phe Leu Lys Ser Gly Asp Ala Ala Ile
                245                 250                 255
Val Asp Met Val Pro Gly Lys Pro Met Cys Val Glu Ser Phe Ser Asp
            260                 265                 270
Tyr Pro Pro Leu Gly Arg Phe Ala Val Arg Asp Met Arg Gln Thr Val
        275                 280                 285
Ala Val Gly Val Ile Lys Ala Val Asp Lys Lys Ala Ala Gly Ala Gly
    290                 295                 300
Lys Val Thr Lys Ser Ala Gln Lys Ala Gln Lys Ala Lys
305                 310                 315
```

<210> SEQ ID NO: 21
<211> LENGTH: 384
<212> TYPE: DNA
<213> ORGANISM: Mouse
<220> FEATURE:
<221> NAME/KEY: unsure
<222> LOCATION: (369)...(369)

<400> SEQUENCE: 21

```
ggtggacttc ggtgggacaa cgtccttcca gtgcaaggtg cgcagtgacg tgaagcctgt      60
gatccagtgg ctgaagcggg tggagtacgg ctccgaggga cgccacaact ccaccattga     120
tgtgggtggc cagaagtttg tggtgttgcc cacgggtgat gtgtggtcac ggcctgatgg     180
ctcctacctc aacaagctgc tcatctctcg ggcccgccag gatgatgctg gcatgtacat     240
ctgcctaggt gcaaatacca tgggctacag tttccgtagc gccttcctca ctgtattacc     300
agaccccaaa cctccagggc tcctatggcc ttcttcatcg tcatccacaa gcctgccatg     360
gcctgtggng atcggcatcc cagc                                            384
```

<210> SEQ ID NO: 22
<211> LENGTH: 1967
<212> TYPE: DNA
<213> ORGANISM: Mouse

<400> SEQUENCE: 22

```
gctgcgcgcc cccgcgctga tccctgtcga gcgtctacgc gcctcgcttc ctttgcctgg      60
agctcggcgc cgaggggggc cggaccctgg ctctgcggcc gcgacctggg tcttgcgggc     120
ctgagccctg agtggcgtcc agtccagctc ccagtgaccg cgcccctgct tcaggtccga     180
ccggcgagat gacgcggagc cccgcgctgc tgctgctgct attgggggcc ctcccgtcgg     240
```

-continued

```
ctgaggcggc gcgaggaccc ccaagaatgg cagacaaagt ggtcccacgg caggtggccc      300
gcctgggccg cactgtgcgg ctacagtgcc cagtggaggg ggacccacca ccgttgacca      360
tgtggaccaa agatggccgc acaatccaca gtggctggag ccgcttccgt gtgctgcccc      420
agggtctgaa ggtgaaggag gtggaggccg aggatgccgg tgtttatgtg tgcaaggcca      480
ccaatggctt tggcagcctc agcgtcaact acactctcat catcatggat gatattagtc      540
cagggaagga gagccctggg ccaggtggtt cttcgggggg ccaggaggac ccagccagcc      600
agcagtgggc acgcctcgc ttcacacagc cctccaagat gaggcgccga gtgattgcac       660
ggcctgtggg tagctctgtg cggctcaagt gtgtggccag tgggcaccca cggccagaca      720
tcatgtggat gaaggatgac cagaccttga cgcatctaga ggctagtgaa cacagaaaga      780
agaagtggac actgagcttg aagaacctga agcctgaaga cagtggcaag tacacgtgcc      840
gtgtatctaa caaggccggt gccatcaacc ccacctacaa agtggatgta atccagcgga      900
ctcgttccaa gcctgtgctc acagggacac accctgtgaa cacaacggtg gacttcggtg      960
ggacaacgtc cttccagtgc aaggtgcgca gtgacgtgaa gcctgtgatc cagtggctga      1020
agcgggtgga gtacggctcc gagggacgcc acaactccac cattgatgtg ggtggccaga     1080
agtttgtggt gttgcccacg ggtgatgtgt ggtcacggcc tgatggctcc tacctcaaca     1140
agctgctcat ctctcgggcc cgccaggatg atgctggcat gtacatctgc ctaggtgcaa     1200
ataccatggg ctacagtttc cgtagcgcct tcctcactgt attaccagac cccaaacctc     1260
cagggcctcc tatggcttct tcatcgtcat ccacaagcct gccatggcct gtggtgatcg     1320
gcatcccagc tggtgctgtc ttcatcctag gcactgtgct gctctggctt gccagacca     1380 agaagaagcc atgtgcccca gcatctacac ttcctgtgcc tgggcatcgt cccccaggga     1440
catcccgaga acgcagtggt gacaaggacc tgccctcatt ggctgtgggc atatgtgagg    1500
agcatggatc cgccatggcc ccccagcaca tcctggcctc tggctcaact gctggcccca     1560
agctgtaccc caagctatac acagatgtgc acacacacac acatacacac acctgcactc     1620
acacgctctc atgtggaggg caaggttcat caacaccagc atgtccacta tcagtgctaa     1680
atacagcgaa tctccaagca ctgtgtcctg aggtaggcat atgggggcca aggcaacagg     1740
ttgggagaat tgagaacaat ggaggaagag tatcttaggg tgccttatgg tggacactca     1800
caaacttggc catatagatg tatgtactac cagatgaaca gccagccaga ttcacacacg     1860
cacatgttta aacgtgtaaa cgtgtgcaca actgcacaca caacctgaga aaccttcagg     1920
aggatttggg gtgtgacttt gcagtgacat gtagcgatgg ctagttg                   1967
```

<210> SEQ ID NO: 23
<211> LENGTH: 1742
<212> TYPE: DNA
<213> ORGANISM: Mouse

<400> SEQUENCE: 23

```
gcgcggcgcc ccgggcccct cgccccgccg cccctcttcc ccgccctcgc caagcctcgc       60
cgtttatccg cgcggacagc gcgccccgcg ccccagcccg gccctagccg ccagcgccca      120
ggtagcgccg ccccgcccag gccgggcccg gggcgcgggc gggcgggatg cggcgcccgg     180
ggcagcgatg accgcgtcgc gctgctcagg ggcccggctc tgaccccgtt gcctgctgcg     240
cgcccccgcg ctgatccctg tcgagcgtct acgcgcctcg cttcctttgc ctggagctcg     300
gcgccgaggg gggccggacc ctggctctgc ggccgcgacc tgggtcttgc gggcctgagc     360
cctgagtggc gtccagtcca gctcccagtg accgcgcccc tgcttcaggt ccgaccggcg     420
```

-continued

```
agatgacgcg gagccccgcg ctgctgctgc tgctattggg ggcccctccg tcggctgagg    480
cggcgcgaga tgatattagt ccagggaagg agagccctgg gccaggtggt tcttcggggg    540
gccaggagga cccagccagc cagcagtggg cacggcctcg cttcacacag ccctccaaga    600
tgaggcgccg agtgattgca cggcctgtgg gtagctctgt gcggctcaag tgtgtggcca    660
gtgggcaccc acggccagac atcatgtgga tgaaggatga ccagaccttg acgcatctag    720
aggctagtga acacagaaag aagaagtgga cactgagctt gaagaacctg aagcctgaag    780
acagtggcaa gtacacgtgc cgtgtatcta caaggccgg tgccatcaac gccacctaca     840
aagtggatgt aatccagcgg actcgttcca agcctgtgct cacagggaca caccctgtga    900
acacaacggt ggacttcggt gggacaacgt ccttccagtg caaggtgcgc agtgacgtga    960
agcctgtgat ccagtggctg aagcgggtgg agtacggctc cgagggacgc cacaactcca   1020
ccattgatgt gggtggccag aagtttgtgg tgttgcccac gggtgatgtg tggtcacggc   1080
ctgatggctc ctacctcaac aagctgctca tctctcgggc ccgccaggat gatgctggca   1140
tgtacatctg cctaggtgca ataccatgg gctacagttt ccgtagcgcc ttcctcactg    1200
tattaccaga ccccaaacct cctccagggc ctcctatggc ttcttcatcg tcatccacaa   1260
gcctgccatg gcctgtggtg atcggcatcc cagctggtgc tgtcttcatc ctaggcactg   1320
tgctgctctg gctttgccag accaagaaga agccatgtgc cccagcatct acacttcctg   1380
tgcctgggca tcgtccccca gggacatccc gagaacgcag tggtgacaag gacctgccct   1440
cattggctgt gggcatatgt gaggagcatg gatccgccat ggccccccag cacatcctgg   1500
cctctggctc aactgctggc cccaagctgt accccaagct atacacagat gtgcacacac   1560
acacacatac acacacctgc actcacacgc tctcatgtgg agggcaaggt tcatcaaac   1620
cagcatgtcc actatcagtg ctaaatacag cgaatctcca agcactgtgt cctgaggtag   1680
gcatatgggg gccaaggcaa caggttggga gaattgagaa caatggagga agagtatctt   1740
ag                                                                  1742
```

<210> SEQ ID NO: 24
<211> LENGTH: 1004
<212> TYPE: DNA
<213> ORGANISM: Human

<400> SEQUENCE: 24

```
gcggccgcga cccaggtcc ggacaggccg agatgacgcc gagcccctg ttgctgctcc      60
tgctgccgcc gctgctgctg ggggccttcc caccggccgc cgccgcccga ggccccccaa    120
agatggcgga caaggtggtc ccacggcagg tggccggctg gccgcactg tgcggctgca     180
gtgccagtgg aggggacccc gccgccgctg accatgtgga ccaaggatgg ccgcaccatc    240
cacagcggct ggaccgcttc cgcgtgctgc cgcaggggc tgaaggtgaa gcaggtggag     300
cgggaggatg ccggcgtgta cgtgtgcaag gccaccaacg gcttcggcag ccttagcgtc    360
aactacaccc tcgtcgtgct ggatgacatt agcccaggga aggagagcct ggggcccgac    420
agctcctctg ggggtcaaga ggaccccgcc agccagcagt gggcacgacc gcgcttcaca    480
cagccctcca agatgaggcg ccgggtgatc gcacggcccg tgggtagctc cgtgcggctc    540
aagtgcgtgg ccagcgggca ccctcggccc gacatcacgt ggatgaagga cgaccaggcc    600
ttgacgcgcc cagaggccgc tgagcccagg aagaagaagt ggacactgag cctgaagaac    660
ctgcggccga aggacagcgg caaatacacc tgccgcgtgt cgaaccgcgc gggcgccatc    720
aacgccacct acaaggtgga tgtgatccag cggacccgtt ccaagcccgt gctcacaggc    780
```

```
acgcaccccg tgaacacgac ggtggacttc ggggggacca cgtccttcca gtgcaaggtg       840
cgcagcgacg tgaagccggt gatccagtgg ctgaagcgcg tggagtacgg cgccgagggc       900
cgccacaact ccaccatcga tgtgggcggc cagaagtttg tggtgctgcc cacgggtgac       960
gtgtggtcgc ggcccgacgg ctcctacctc aataagccgc tccc                       1004

<210> SEQ ID NO: 25
<211> LENGTH: 478
<212> TYPE: DNA
<213> ORGANISM: Mouse

<400> SEQUENCE: 25
agaaaaaggc ctcgctaaag caacaaacct gatcattttc aagaaccata ggactgaggt        60
gaagccatga agttcttgct gatctcccta gccctatggc tgggcacagt gggcacacgt       120
gggacagagc ccgaactcag cgagacccag cgcaggagcc tacaggtggc tctggaggag       180
ttccacaaac acccacctgt gcagttggcc ttccaagaga tcggtgtgga cagagctgaa       240
gaagtgctct tctcagctgg cacctttgtg aggttggaat ttaagctcca gcagaccaac       300
tgccccaaga aggactggaa aaagccggag tgcacaatca aaccaaacgg ggcggaaatg       360
cctggcctgc attaaaatgg accccaaggg taaaattcta ggccggatag tccactgccc       420
aattctgaag caagggcctc aggatcctca ggagttgcaa tgcattaaga tagcacag        478

<210> SEQ ID NO: 26
<211> LENGTH: 545
<212> TYPE: DNA
<213> ORGANISM: Mouse

<400> SEQUENCE: 26
agggaacaac tgccagggag ctgttccagg gaccacacag aaaaaggcct cgctaaagca        60
acaaacctga tcattttcaa gaaccatagg actgaggtga agccatgaag ttcttgctga       120
tctccctagc cctatggctg ggcacagtgg gcacacgtgg gacagagccc gaactcagcg       180
agacccagcg caggagccta caggtggctc tggaggagtt ccacaaacac ccacctgtgc       240
agttggcctt ccaagagatc ggtgtggaca gagctgaaga agtgctcttc tcagctggca       300
cctttgtgag gttggaattt aagctccagc agaccaactg ccccaagaag gactggaaaa       360
agccggagtg cacaatcaaa ccaaacggga aggcggaaat gcctggcctg cattaaaaat       420 ggaccccaa gggtaaaatt ctaggccgga tagtccactg cccaattctg aagcaagggc       480
ctcaggatcc tcaggagttg caatgcatta agatagcaca ggctggcgaa gacccccacg       540
gctac                                                                   545

<210> SEQ ID NO: 27
<211> LENGTH: 2213
<212> TYPE: DNA
<213> ORGANISM: Mouse

<400> SEQUENCE: 27
gttgcaggcg ctcggagtca gcatggaaag tctctgcggg gtcctgggat ttctgctgct        60
ggctgcagga ctgcctctcc aggctgccaa gcgatttcgt gatgtgctgg ccatgaaca       120 gtatcccaat cacatgagag agcacaacca attacgtggc tggtcttcgg atgaaaatga       180
atgggatgaa cacctgtatc cagtgtggag gagggagac ggcaggtgga aggactcctg       240
ggaaggaggc cgtgtgcagg cagtcctgac cagtgactca ccggctctgg tgggttccaa       300
tatcaccttt gtggtgaacc tggtgttccc cagatgccag aaggaagatg ctaatggcaa       360
```

-continued

```
tatcgtctat gagaagaact gcaggaatga tttgggactg acctctgacc tgcatgtcta    420
caactggact gcaggggcag atgatggtga ctgggaagat ggcaccagcc gaagccagca    480
tctcaggttc ccggacagga ggcccttccc tcgcccccat ggatgaaga aatggagctt     540 tgtctacgtc tttcacacac ttggccagta tttccaaaaa ctgggtcggt gttcagcacg    600
ggtttctata aacacagtca acttgacagc tggccctcag gtcatggaag tgactgtctt    660
tcgaagatac ggccgggcat acattccat ctcgaaggtg aaagatgtgt atgtgataac     720
agatcagatc cctgtattcg tgaccatgtc ccagaagaat gacaggaact tgtctgatga    780
gatcttcctc agagacctcc ccatcgtctt cgatgtcctc attcatgatc ccagccactt    840
cctcaacgac tctgccattt cctacaagtg aactttggg acaacactg gcctgtttgt      900 ctccaacaat cacactttga atcacactta tgtgctcaat ggaaccttca accttaacct    960
caccgtgcaa actgcagtgc ccgggccatg ccctcccct tcgccttcga ctccgcctcc     1020
accttcaact ccgccctcac ctccgccctc acctctgccc acattatcaa cacctagccc    1080
ctctttaatg cctactggtt acaaatccat ggagctgagt gacatttcca atgaaaactg    1140
ccgaataaac agatatggct acttcagagc caccatcaca attgtagagg ggatcctgga    1200
agtcagcatc atgcagatag cagatgtccc catgcccaca ccgcagcctg ccaactccct    1260
gatggacttc actgtgacct gcaaagggggc cacccccatg gaagcctgta cgatcatctc    1320
cgaccccacc tgccagatcg cccagaaccg ggtctgcagc cctgtggctg tggatgggct    1380
gtgcctgctg tctgtgagaa gagccttcaa tgggtctggc acctactgtg tgaatttcac    1440
tctgggagat gatgcaagcc tggccctcac cagcaccctg atctctatcc ctggcaaaga    1500
cccagactcc cctctgagag cagtgaatgg tgtcctgatc tccattggct gcctggctgt    1560
gcttgtcacc atggttacca tcttgctgta caaaaaacac aaggcgtaca agccaatagg    1620
aaactgcccc aggaacacgg tcaagggcaa aggcctgagt gttctcctca gccacgcgaa    1680
agccccgttc ttccgaggag accaggagaa ggatccattg ctccaggaca agccaaggac    1740
actctaagtc tttggccttc cctctgacca ggaacccact cttctgtgca tgtatgtgag    1800
ctgtgcagaa gtatgtggct gggaactgtt gttctctaag gattattgta aaatgtatat    1860
cgtggcttag ggagtgtggt taaatagcat tttagagaag acatgggaag acttagtgtt    1920
tcttcccatc tgtattgtgg tttttacact gttcgtgggg tggacacgct gtgtctgaag    1980
gggaggtggg gtcactgcta cttaaggtcc taggttaact gggggagata ccacagatgc    2040
ctcagctttc cacataacat gggcatgaac ccagctaatc accacctgaa ggccatgctt    2100 catctgccctt ccaactcact gagcatgcct gagctcctga caaaattata atgggcccgg    2160
gctttgtgta tggtgcgtgt gtgtacatat tctactcatt aaaaaggtag tct            2213
```

<210> SEQ ID NO: 28
<211> LENGTH: 412
<212> TYPE: DNA
<213> ORGANISM: Mouse

<400> SEQUENCE: 28

```
gcggagtccc gcctcgccgc ccctcgagcg ccccagcttc tctgctggc cggaacctgc     60 accccgaacc aggaagcacc tggcggcggg cgcgggatgg ctgggcccag ctggggtctc    120
cctcggctgg acggtttcat ccttaccgag cgctgggca gtggcacgta cgccacggtg    180
tacaaggcct acgccaagaa ggatactcgg gaagtggtag ccataaaatg cgtggccaag    240
aagagtctca acaaggcgtc agtggaaaac ctcctgactg agattgagat cctcaagggc    300
```

-continued

```
attcggcacc cccatatcgt gcagctgaaa gacttccagt gggacaatga caatatctac    360
ctcatcatgg agttctgtgc aggggqtgac ctgtctcgct tcattcatac cc            412
```

<210> SEQ ID NO: 29
<211> LENGTH: 437
<212> TYPE: DNA
<213> ORGANISM: Mouse
<400> SEQUENCE: 29

```
cacagtcttg tttctggtgg ctttgatcac tgtggggatg aacactacct atgtagtgtc     60
ttgccccaaa gaatttgaaa acctggagc ttgtcccaag ccttcaccag aaagtgttgg    120
aatttgtgtt gatcaatgct caggagatgg atcctgccct ggcaacatga agtgctgtag   180
caatagctgt ggtcatgtct gcaaaactcc tgtcttttaa atggttgaca gccatgtgga   240
agatggattc aatcttcata acatgaatg atggccagcc ccagaagatt tcttctgaat    300
tcacagagcc tgtgcttggc tacttcctag ccctagaatt gcattcttgg acaaggaaga   360
tctatattgt ggtgacaatg ccctaatatg tctgtgtcca aaataaacta cccttagcat    420
tcaaaaaaaa aaaaaaa                                                   437
```

<210> SEQ ID NO: 30
<211> LENGTH: 126
<212> TYPE: PRT
<213> ORGANISM: Mouse
<220> FEATURE:
<221> NAME/KEY: UNSURE
<222> LOCATION: (123)...(123)

<400> SEQUENCE: 30

```
Val Asp Phe Gly Gly Thr Thr Ser Phe Gln Cys Lys Val Arg Ser Asp
 1               5                  10                  15

Val Lys Pro Val Ile Gln Trp Leu Lys Arg Val Glu Tyr Gly Ser Glu
            20                  25                  30

Gly Arg His Asn Ser Thr Ile Asp Val Gly Gln Lys Phe Val Val
        35                  40                  45

Leu Pro Thr Gly Asp Val Trp Ser Arg Pro Asp Gly Ser Tyr Leu Asn
    50                  55                  60

Lys Leu Leu Ile Ser Arg Ala Arg Gln Asp Asp Ala Gly Met Tyr Ile
65                  70                  75                  80

Cys Leu Gly Ala Asn Thr Met Gly Tyr Ser Phe Arg Ser Ala Phe Leu
                85                  90                  95

Thr Val Leu Pro Asp Pro Lys Pro Pro Gly Pro Pro Met Ala Ser Ser
               100                 105                 110

Ser Ser Ser Thr Ser Leu Pro Trp Pro Val Xaa Gly Ile Pro
           115                 120                 125
```

<210> SEQ ID NO: 31
<211> LENGTH: 529
<212> TYPE: PRT
<213> ORGANISM: Mouse
<400> SEQUENCE: 31

```
Met Thr Arg Ser Pro Ala Leu Leu Leu Leu Leu Gly Ala Leu Pro
 1               5                  10                  15

Ser Ala Glu Ala Ala Arg Gly Pro Pro Arg Met Ala Asp Lys Val Val
            20                  25                  30

Pro Arg Gln Val Ala Arg Leu Gly Arg Thr Val Arg Leu Gln Cys Pro
        35                  40                  45
```

-continued

```
Val Glu Gly Asp Pro Pro Leu Thr Met Trp Thr Lys Asp Gly Arg
    50                  55                  60

Thr Ile His Ser Gly Trp Ser Arg Phe Arg Val Leu Pro Gln Gly Leu
65                  70                  75                  80

Lys Val Lys Glu Val Glu Ala Glu Asp Ala Gly Val Tyr Val Cys Lys
                85                  90                  95

Ala Thr Asn Gly Phe Gly Ser Leu Ser Val Asn Tyr Thr Leu Ile Ile
            100                 105                 110

Met Asp Asp Ile Ser Pro Gly Lys Glu Ser Pro Gly Pro Gly Gly Ser
            115                 120                 125

Ser Gly Gly Gln Glu Asp Pro Ala Ser Gln Gln Trp Ala Arg Pro Arg
    130                 135                 140

Phe Thr Gln Pro Ser Lys Met Arg Arg Val Ile Ala Arg Pro Val
145                 150                 155                 160

Gly Ser Ser Val Arg Leu Lys Cys Val Ala Ser Gly His Pro Arg Pro
                165                 170                 175

Asp Ile Met Trp Met Lys Asp Asp Gln Thr Leu Thr His Leu Glu Ala
            180                 185                 190

Ser Glu His Arg Lys Lys Lys Trp Thr Leu Ser Leu Lys Asn Leu Lys
    195                 200                 205

Pro Glu Asp Ser Gly Lys Tyr Thr Cys Arg Val Ser Asn Lys Ala Gly
    210                 215                 220

Ala Ile Asn Ala Thr Tyr Lys Val Asp Val Ile Gln Arg Thr Arg Ser
225                 230                 235                 240

Lys Pro Val Leu Thr Gly Thr His Pro Val Asn Thr Thr Val Asp Phe
                245                 250                 255

Gly Gly Thr Thr Ser Phe Gln Cys Lys Val Arg Ser Asp Val Lys Pro
            260                 265                 270

Val Ile Gln Trp Leu Lys Arg Val Glu Tyr Gly Ser Glu Gly Arg His
        275                 280                 285

Asn Ser Thr Ile Asp Val Gly Gly Gln Lys Phe Val Val Leu Pro Thr
    290                 295                 300

Gly Asp Val Trp Ser Arg Pro Asp Gly Ser Tyr Leu Asn Lys Leu Leu
305                 310                 315                 320

Ile Ser Arg Ala Arg Gln Asp Asp Ala Gly Met Tyr Ile Cys Leu Gly
                325                 330                 335

Ala Asn Thr Met Gly Tyr Ser Phe Arg Ser Ala Phe Leu Thr Val Leu
            340                 345                 350

Pro Asp Pro Lys Pro Pro Gly Pro Pro Met Ala Ser Ser Ser Ser Ser
        355                 360                 365

Thr Ser Leu Pro Trp Pro Val Val Ile Gly Ile Pro Ala Gly Ala Val
    370                 375                 380

Phe Ile Leu Gly Thr Val Leu Leu Trp Leu Cys Gln Thr Lys Lys Lys
385                 390                 395                 400

Pro Cys Ala Pro Ala Ser Thr Leu Pro Val Pro Gly His Arg Pro Pro
                405                 410                 415

Gly Thr Ser Arg Glu Arg Ser Gly Asp Lys Asp Leu Pro Ser Leu Ala
            420                 425                 430

Val Gly Ile Cys Glu Glu His Gly Ser Ala Met Ala Pro Gln His Ile
        435                 440                 445

Leu Ala Ser Gly Ser Thr Ala Gly Pro Lys Leu Tyr Pro Lys Leu Tyr
450                 455                 460
```

```
Thr Asp Val His Thr His Thr His Thr Cys Thr His Thr Leu
465                 470                475                480

Ser Cys Gly Gly Gln Gly Ser Ser Thr Pro Ala Cys Pro Leu Ser Val
            485                 490                495

Leu Asn Thr Ala Asn Leu Gln Ala Leu Cys Pro Glu Val Gly Ile Trp
            500                 505                510

Gly Pro Arg Gln Gln Val Gly Arg Ile Glu Asn Asn Gly Gly Arg Val
            515                 520                525

Ser

<210> SEQ ID NO: 32
<211> LENGTH: 439
<212> TYPE: PRT
<213> ORGANISM: Mouse

<400> SEQUENCE: 32

Met Thr Arg Ser Pro Ala Leu Leu Leu Leu Leu Gly Ala Leu Pro
1               5                   10                  15

Ser Ala Glu Ala Ala Arg Asp Asp Ile Ser Pro Gly Lys Glu Ser Pro
            20                  25                  30

Gly Pro Gly Gly Ser Ser Gly Gly Gln Glu Asp Pro Ala Ser Gln Gln
            35                  40                  45

Trp Ala Arg Pro Arg Phe Thr Gln Pro Ser Lys Met Arg Arg Val
50                  55                  60

Ile Ala Arg Pro Val Gly Ser Ser Val Arg Leu Lys Cys Val Ala Ser
65                  70                  75                  80

Gly His Pro Arg Pro Asp Ile Met Trp Met Lys Asp Asp Gln Thr Leu
            85                  90                  95

Thr His Leu Glu Ala Ser Glu His Arg Lys Lys Lys Trp Thr Leu Ser
            100                 105                 110

Leu Lys Asn Leu Lys Pro Glu Asp Ser Gly Lys Tyr Thr Cys Arg Val
            115                 120                 125

Ser Asn Lys Ala Gly Ala Ile Asn Ala Thr Tyr Lys Val Asp Val Ile
            130                 135                 140

Gln Arg Thr Arg Ser Lys Pro Val Leu Thr Gly Thr His Pro Val Asn
145                 150                 155                 160

Thr Thr Val Asp Phe Gly Gly Thr Thr Ser Phe Gln Cys Lys Val Arg
            165                 170                 175

Ser Asp Val Lys Pro Val Ile Gln Trp Leu Lys Arg Val Glu Tyr Gly
            180                 185                 190

Ser Glu Gly Arg His Asn Ser Thr Ile Asp Val Gly Gly Gln Lys Phe
            195                 200                 205

Val Val Leu Pro Thr Gly Asp Val Trp Ser Arg Pro Asp Gly Ser Tyr
210                 215                 220

Leu Asn Lys Leu Leu Ile Ser Arg Ala Arg Gln Asp Asp Ala Gly Met
225                 230                 235                 240

Tyr Ile Cys Leu Gly Ala Asn Thr Met Gly Tyr Ser Phe Arg Ser Ala
            245                 250                 255

Phe Leu Thr Val Leu Pro Asp Pro Lys Pro Pro Gly Pro Pro Met
            260                 265                 270

Ala Ser Ser Ser Ser Thr Ser Leu Pro Trp Pro Val Val Ile Gly
            275                 280                 285

Ile Pro Ala Gly Ala Val Phe Ile Leu Gly Thr Val Leu Leu Trp Leu
            290                 295                 300
```

```
Cys Gln Thr Lys Lys Lys Pro Cys Ala Pro Ala Ser Thr Leu Pro Val
305                 310                 315                 320

Pro Gly His Arg Pro Gly Thr Ser Arg Glu Arg Ser Gly Asp Lys
            325                 330                 335

Asp Leu Pro Ser Leu Ala Val Gly Ile Cys Glu Glu His Gly Ser Ala
                340                 345                 350

Met Ala Pro Gln His Ile Leu Ala Ser Gly Ser Thr Ala Gly Pro Lys
            355                 360                 365

Leu Tyr Pro Lys Leu Tyr Thr Asp Val His Thr His Thr His Thr His
    370                 375                 380

Thr Cys Thr His Thr Leu Ser Cys Gly Gly Gln Gly Ser Ser Thr Pro
385                 390                 395                 400

Ala Cys Pro Leu Ser Val Leu Asn Thr Ala Asn Leu Gln Ala Leu Cys
                405                 410                 415

Pro Glu Val Gly Ile Trp Gly Pro Arg Gln Gln Val Gly Arg Ile Glu
            420                 425                 430

Asn Asn Gly Gly Arg Val Ser
            435

<210> SEQ ID NO: 33
<211> LENGTH: 322
<212> TYPE: PRT
<213> ORGANISM: Human

<400> SEQUENCE: 33

Arg Arg Ala Pro Cys Cys Ser Cys Cys Arg Arg Cys Cys Trp Gly
1               5                   10                  15

Pro Ser His Arg Pro Pro Pro Glu Ala Pro Gln Arg Trp Arg Thr
            20                  25                  30

Arg Trp Ser His Gly Arg Trp Pro Ala Gly Pro His Cys Ala Ala Ala
            35                  40                  45

Val Pro Val Glu Gly Asp Pro Pro Leu Thr Met Trp Thr Lys Asp
    50                  55                  60

Gly Arg Thr Ile His Ser Gly Trp Ser Arg Phe Arg Val Leu Pro Gln
65                  70                  75                  80

Gly Leu Lys Val Lys Gln Val Glu Arg Glu Asp Ala Gly Val Tyr Val
                85                  90                  95

Cys Lys Ala Thr Asn Gly Phe Gly Ser Leu Ser Val Asn Tyr Thr Leu
                100                 105                 110

Val Val Leu Asp Asp Ile Ser Pro Gly Lys Glu Ser Leu Gly Pro Asp
            115                 120                 125

Ser Ser Gly Gly Gln Glu Asp Pro Ala Ser Gln Gln Trp Ala Arg
            130                 135                 140

Pro Arg Phe Thr Gln Pro Ser Lys Met Arg Arg Val Ile Ala Arg
145                 150                 155                 160

Pro Val Gly Ser Ser Val Arg Leu Lys Cys Val Ala Ser Gly His Pro
                165                 170                 175

Arg Pro Asp Ile Thr Trp Met Lys Asp Gln Ala Leu Thr Arg Pro
            180                 185                 190

Glu Ala Ala Glu Pro Arg Lys Lys Lys Trp Thr Leu Ser Leu Lys Asn
    195                 200                 205

Leu Arg Pro Glu Asp Ser Gly Lys Tyr Thr Cys Arg Val Ser Asn Arg
    210                 215                 220

Ala Gly Ala Ile Asn Ala Thr Tyr Lys Val Asp Val Ile Gln Arg Thr
225                 230                 235                 240
```

```
Arg Ser Lys Pro Val Leu Thr Gly Thr His Pro Val Asn Thr Thr Val
                245                 250                 255

Asp Phe Gly Gly Thr Thr Ser Phe Gln Cys Lys Val Arg Ser Asp Val
                260                 265                 270

Lys Pro Val Ile Gln Trp Leu Lys Arg Val Glu Tyr Gly Ala Glu Gly
                275                 280                 285

Arg His Asn Ser Thr Ile Asp Val Gly Gly Gln Lys Phe Val Val Leu
                290                 295                 300

Pro Thr Gly Asp Val Trp Ser Arg Pro Asp Gly Ser Tyr Leu Asn Lys
305                 310                 315                 320

Pro Leu

<210> SEQ ID NO: 34
<211> LENGTH: 102
<212> TYPE: PRT
<213> ORGANISM: Mouse

<400> SEQUENCE: 34

Met Lys Phe Leu Leu Ile Ser Leu Ala Leu Trp Leu Gly Thr Val Gly
  1               5                  10                  15

Thr Arg Gly Thr Glu Pro Glu Leu Ser Glu Thr Gln Arg Arg Ser Leu
                 20                  25                  30

Gln Val Ala Leu Glu Glu Phe His Lys His Pro Pro Val Gln Leu Ala
             35                  40                  45

Phe Gln Glu Ile Gly Val Asp Arg Ala Glu Glu Val Leu Phe Ser Ala
         50                  55                  60

Gly Thr Phe Val Arg Leu Glu Phe Lys Leu Gln Gln Thr Asn Cys Pro
 65                  70                  75                  80

Lys Lys Asp Trp Lys Lys Pro Glu Cys Thr Ile Lys Pro Asn Gly Ala
                 85                  90                  95

Glu Met Pro Gly Leu His
            100

<210> SEQ ID NO: 35
<211> LENGTH: 147
<212> TYPE: PRT
<213> ORGANISM: Mouse

<400> SEQUENCE: 35

Met Lys Phe Leu Leu Ile Ser Leu Ala Leu Trp Leu Gly Thr Val Gly
  1               5                  10                  15

Thr Arg Gly Thr Glu Pro Glu Leu Ser Glu Thr Gln Arg Arg Ser Leu
                 20                  25                  30

Gln Val Ala Leu Glu Glu Phe His Lys His Pro Pro Val Gln Leu Ala
             35                  40                  45

Phe Gln Glu Ile Gly Val Asp Arg Ala Glu Glu Val Leu Phe Ser Ala
         50                  55                  60

Gly Thr Phe Val Arg Leu Glu Phe Lys Leu Gln Gln Thr Asn Cys Pro
 65                  70                  75                  80

Lys Lys Asp Trp Lys Lys Pro Glu Cys Thr Ile Lys Pro Asn Gly Arg
                 85                  90                  95

Arg Arg Lys Cys Leu Ala Cys Ile Lys Met Asp Pro Lys Gly Lys Ile
            100                 105                 110

Leu Gly Arg Ile Val His Cys Pro Ile Leu Lys Gln Gly Pro Gln Asp
            115                 120                 125
```

-continued

```
Pro Gln Glu Leu Gln Cys Ile Lys Ile Ala Gln Ala Gly Glu Asp Pro
        130                 135                 140

His Gly Tyr
145

<210> SEQ ID NO: 36
<211> LENGTH: 574
<212> TYPE: PRT
<213> ORGANISM: Mouse

<400> SEQUENCE: 36

Met Glu Ser Leu Cys Gly Val Leu Gly Phe Leu Leu Ala Ala Gly
 1               5                  10                  15

Leu Pro Leu Gln Ala Ala Lys Arg Phe Arg Asp Val Leu Gly His Glu
                20                  25                  30

Gln Tyr Pro Asn His Met Arg Glu His Asn Gln Leu Arg Gly Trp Ser
            35                  40                  45

Ser Asp Glu Asn Glu Trp Asp Glu His Leu Tyr Pro Val Trp Arg Arg
    50                  55                  60

Gly Asp Gly Arg Trp Lys Asp Ser Trp Glu Gly Gly Arg Val Gln Ala
65                  70                  75                  80

Val Leu Thr Ser Asp Ser Pro Ala Leu Val Gly Ser Asn Ile Thr Phe
                85                  90                  95

Val Val Asn Leu Val Phe Pro Arg Cys Gln Lys Glu Asp Ala Asn Gly
                100                 105                 110

Asn Ile Val Tyr Glu Lys Asn Cys Arg Asn Asp Leu Gly Leu Thr Ser
            115                 120                 125

Asp Leu His Val Tyr Asn Trp Thr Ala Gly Ala Asp Asp Gly Asp Trp
    130                 135                 140

Glu Asp Gly Thr Ser Arg Ser Gln His Leu Arg Phe Pro Asp Arg Arg
145                 150                 155                 160

Pro Phe Pro Arg Pro His Gly Trp Lys Lys Trp Ser Phe Val Tyr Val
                165                 170                 175

Phe His Thr Leu Gly Gln Tyr Phe Gln Lys Leu Gly Arg Cys Ser Ala
            180                 185                 190

Arg Val Ser Ile Asn Thr Val Asn Leu Thr Ala Gly Pro Gln Val Met
        195                 200                 205

Glu Val Thr Val Phe Arg Arg Tyr Gly Arg Ala Tyr Ile Pro Ile Ser
    210                 215                 220

Lys Val Lys Asp Val Tyr Val Ile Thr Asp Gln Ile Pro Val Phe Val
225                 230                 235                 240

Thr Met Ser Gln Lys Asn Asp Arg Asn Leu Ser Asp Glu Ile Phe Leu
                245                 250                 255

Arg Asp Leu Pro Ile Val Phe Asp Val Leu Ile His Asp Pro Ser His
            260                 265                 270

Phe Leu Asn Asp Ser Ala Ile Ser Tyr Lys Trp Asn Phe Gly Asp Asn
        275                 280                 285

Thr Gly Leu Phe Val Ser Asn Asn His Thr Leu Asn His Thr Tyr Val
    290                 295                 300

Leu Asn Gly Thr Phe Asn Leu Asn Leu Thr Val Gln Thr Ala Val Pro
305                 310                 315                 320

Gly Pro Cys Pro Pro Ser Pro Ser Thr Pro Pro Pro Ser Thr
                325                 330                 335

Pro Pro Ser Pro Pro Ser Pro Leu Pro Thr Leu Ser Thr Pro Ser
            340                 345                 350
```

-continued

Pro Ser Leu Met Pro Thr Gly Tyr Lys Ser Met Glu Leu Ser Asp Ile
            355                 360                 365

Ser Asn Glu Asn Cys Arg Ile Asn Arg Tyr Gly Tyr Phe Arg Ala Thr
        370                 375                 380

Ile Thr Ile Val Glu Gly Ile Leu Glu Val Ser Ile Met Gln Ile Ala
385                 390                 395                 400

Asp Val Pro Met Pro Thr Pro Gln Pro Ala Asn Ser Leu Met Asp Phe
                405                 410                 415

Thr Val Thr Cys Lys Gly Ala Thr Pro Met Glu Ala Cys Thr Ile Ile
            420                 425                 430

Ser Asp Pro Thr Cys Gln Ile Ala Gln Asn Arg Val Cys Ser Pro Val
            435                 440                 445

Ala Val Asp Gly Leu Cys Leu Leu Ser Val Arg Arg Ala Phe Asn Gly
    450                 455                 460

Ser Gly Thr Tyr Cys Val Asn Phe Thr Leu Gly Asp Asp Ala Ser Leu
465                 470                 475                 480

Ala Leu Thr Ser Thr Leu Ile Ser Ile Pro Gly Lys Asp Pro Asp Ser
            485                 490                 495

Pro Leu Arg Ala Val Asn Gly Val Leu Ile Ser Ile Gly Cys Leu Ala
                500                 505                 510

Val Leu Val Thr Met Val Thr Ile Leu Leu Tyr Lys Lys His Lys Ala
            515                 520                 525

Tyr Lys Pro Ile Gly Asn Cys Pro Arg Asn Thr Val Lys Gly Lys Gly
        530                 535                 540

Leu Ser Val Leu Leu Ser His Ala Lys Ala Pro Phe Phe Arg Gly Asp
545                 550                 555                 560

Gln Glu Lys Asp Pro Leu Leu Gln Asp Lys Pro Arg Thr Leu
                565                 570

<210> SEQ ID NO: 37
<211> LENGTH: 137
<212> TYPE: PRT
<213> ORGANISM: Mouse

<400> SEQUENCE: 37

Ala Glu Ser Arg Leu Ala Ala Pro Arg Ala Pro Pro Ala Ser Leu Leu
1               5                   10                  15

Ala Gly Thr Cys Thr Pro Asn Gln Glu Ala Pro Gly Gly Gly Arg Gly
            20                  25                  30

Met Ala Gly Pro Ser Trp Gly Leu Pro Arg Leu Asp Gly Phe Ile Leu
        35                  40                  45

Thr Glu Arg Leu Gly Ser Gly Thr Tyr Ala Thr Val Tyr Lys Ala Tyr
    50                  55                  60

Ala Lys Lys Asp Thr Arg Glu Val Val Ala Ile Lys Cys Val Ala Lys
65                  70                  75                  80

Lys Ser Leu Asn Lys Ala Ser Val Glu Asn Leu Leu Thr Glu Ile Glu
                85                  90                  95

Ile Leu Lys Gly Ile Arg His Pro His Ile Val Gln Leu Lys Asp Phe
            100                 105                 110

Gln Trp Asp Asn Asp Asn Ile Tyr Leu Ile Met Glu Phe Cys Ala Gly
        115                 120                 125

Gly Asp Leu Ser Arg Phe Ile His Thr
    130                 135

```
<210> SEQ ID NO: 38
<211> LENGTH: 72
<212> TYPE: PRT
<213> ORGANISM: Mouse

<400> SEQUENCE: 38

Thr Val Leu Phe Leu Val Ala Leu Ile Thr Val Gly Met Asn Thr Thr
 1               5                  10                  15

Tyr Val Val Ser Cys Pro Lys Glu Phe Glu Lys Pro Gly Ala Cys Pro
            20                  25                  30

Lys Pro Ser Pro Glu Ser Val Gly Ile Cys Val Asp Gln Cys Ser Gly
        35                  40                  45

Asp Gly Ser Cys Pro Gly Asn Met Lys Cys Cys Ser Asn Ser Cys Gly
    50                  55                  60

His Val Cys Lys Thr Pro Val Phe
65                  70
```

COMPOSITIONS ISOLATED FROM STROMAL CELLS AND METHODS FOR THEIR USE

REFERENCE TO RELATED APPLICATION

This application is a continuation-in-part of U.S. patent application Ser. No. 09/276,268 filed Mar. 25, 1999 now abandoned.

TECHNICAL FIELD OF THE INVENTION

This invention relates to genes encoding proteins expressed in lymph node stromal cells from flaky skin (fsn -/-) mice and their use in therapeutic methods.

BACKGROUND OF THE INVENTION

Lymph vessels and nodes are important components of the body's immune system. Lymph nodes are small lymphatic organs that are located in the path of lymph vessels. Large molecules and cells, including foreign substances, enter into the lymphatic vessels and, in circulating through these vessels, pass through the lymph nodes. Here, any foreign substances are concentrated and exposed to lymphocytes. This triggers a cascade of events that constitute an immune response, protecting the body from infection and from cancer.

Lymph nodes are surrounded by a dense connective tissue network that forms a supporting capsule. This network extends into the body of the lymph node, forming an additional framework of support. Throughout the remainder of the organ, a fine meshwork can be identified that comprises reticular fibres and the reticular cells that produce and surround the fibres. These features provide a support for the main functional cells of the lymphatic system, which are T- and B-lymphocytes. Additional cell types found in lymph nodes include macrophages, follicular dendritic cells, and endothelial cells that line the blood vessels servicing the node.

The cells within lymph nodes communicate with each other in order to defend the body against foreign substances. When a foreign substance, or antigen, is present, it is detected by macrophages and follicular dendritic cells that take up and process the antigen, and display parts of it on their cell surface. These cell surface antigens are then presented to T- and B-lymphocytes, causing them to proliferate and differentiate into activated T-lymphocytes and plasma cells, respectively. These cells are released into the circulation in order to seek out and destroy antigen. Some T- and B-lymphocytes will also differentiate into memory cells. Should these cells come across the same antigen at a later date, the immune response will be more rapid.

Once activated T- and B-lymphocytes are released into the circulation, they can perform a variety of functions that leads to the eventual destruction of antigen. Activated T-lymphocytes can differentiate into cytotoxic lymphocytes (also known as killer T-cells) which recognise other cells that have foreign antigens on their surface and kill the cell by causing them to lyse. Activated T-lymphocytes can also differentiate into helper T-cells which will then secrete proteins in order to stimulate B-lymphocytes, and other T-lymphocytes, to respond to antigens. In addition, activated T-lymphocytes can differentiate into suppressor T-cells which secrete factors that suppress the activity of B-lymphocytes. Activated B-lymphocytes differentiate into plasma cells, which synthesise and secrete antibodies that bind to foreign antigens. The antibody-antigen complex is then detected and destroyed by macrophages, or by a group of blood constituents known as complement.

Lymph nodes can be dissociated and the resulting cells grown in culture. Cells that adhere to the tissue culture dishes can be maintained for some length of time and are known as stromal cells. The cultured cells are a heterogeneous population and can be made up of most cells residing within lymph nodes, such as reticular cells, follicular dendritic cells, macrophages and endothelial cells. It is well known that bone marrow stromal cells play a critical role in homing, growth and differentiation of hematopoietic progenitor cells. Proteins produced by stromal cells are necessary for the maintenance of plasma cells in vitro. Furthermore, stromal cells are known to secrete factors and present membrane-bound receptors that are necessary for the survival of lymphoma cells.

An autosomal recessive mutation, designated flaky skin (fsn -/-), has been described in the inbred A/J mouse strain (The Jackson Laboratory, Bar Harbour, Me.). The mice have a skin disorder similar to psoriasis in humans. Psoriasis is a common disease affecting 2% of the population, which is characterised by a chronic inflammation associated with thickening and scaling of the skin. Histology of skin lesions shows increased proliferation of the cells in the epidermis, the uppermost layer of skin, together with the abnormal presence of inflammatory cells, including lymphocytes, in the dermis, the layer of skin below the epidermis. While the cause of the disease is unclear, psoriasis is associated with a disturbance of the immune system involving T lymphocytes. The disease occurs more frequently in family members, indicating the involvement of a genetic factor as well. Mice with the fsn gene mutation have not only a psoriatic-like skin disease but also other abnormalities involving cells of the immune and hematopoietic system. These mice have markedly increased numbers of lymphocytes associated with enlarged lymphoid organs, including the spleen and lymph nodes. In addition, their livers are enlarged, and the mice are anaemic. Genes and proteins expressed in abnormal lymph nodes of fsn-/- mice may thus influence the development or function of cells of the immune and hematopoietic system, the response of these cells in inflammatory disorders, and the responses of skin and other connective tissue cells to inflammatory signals.

There is a need in the art to identify genes encoding proteins that function to modulate all cells of the immune system. These proteins from normal or abnormal lymph nodes may be useful in modifying the immune responses to tumour cells or infectious agents such as bacteria, viruses, protozoa and worms. Such proteins may be useful in the treatment of disorders where the immune system initiates unfavourable reactions to the body, including Type I hypersensitivity reactions (such as hay fever, eczema, allergic rhinitis and asthma), and Type II hypersensitivity reactions (such as transfusion reactions and haemolytic disease of newborns). Other unfavourable reactions are initiated during Type III reactions, which are due to immune complexes forming in infected organs during persistent infection or in the lungs following repeated inhalation of materials from moulds, plants or animals, and in Type IV reactions in diseases such as leprosy, schistosomiasis and dermatitis.

Novel proteins of the immune system may also be useful in treating autoimmune diseases where the body recognises itself as foreign. Examples of such diseases include rheumatoid arthritis, Addison's disease, ulcerative colitis, dermatomyositis and lupus. Such proteins may also be useful during tissue transplantation, where the body will often recognise the transplanted tissue as foreign and attempt to kill it, and also in bone marrow transplantation when there is a high risk of graft-versus-host disease where the transplanted cells attack their host cells, often causing death.

There thus remains a need in the art for the identification and isolation of genes encoding proteins expressed in cells of the immune system for use in the development of therapeutic agents for the treatment of disorders including those associated with the immune system.

SUMMARY OF THE INVENTION

The present invention provides polypeptides expressed in lymph node stromal cells of fsn -/- mice, together with polynucleotides encoding such polypeptides, expression vectors and host cells comprising such polynucleotides, and methods for their use.

In specific embodiments, isolated polypeptides are provided that comprise an amino acid sequence selected from the group consisting of sequences provided in SEQ ID NO: 11–20 and 30–38, and variants of such sequences, as defined herein. Isolated polypeptides which comprise at least a functional portion of a polypeptide comprising an amino acid sequence selected from the group consisting of: (a) sequences provided in SEQ ID NO: 11–20 and 30–38; and (b) variants of a sequence of SEQ ID NO: 11–20 and 30–38, as defined herein, are also provided.

In other embodiments, the present invention provides isolated polynucleotides comprising a nucleotide sequence selected from the group consisting of: (a) sequences provided in SEQ ID NO: 1–10 and 21–29; (b) complements of sequences provided in SEQ ID NO: 1–10 and 21–29; (c) reverse complements of sequences provided in SEQ ID NO: 1–10 and 21–29; (d) reverse sequences of sequences provided in SEQ ID NO: 1–10 and 21–29; and (e) variants of the sequences of (a)–(d), as defined herein.

In related embodiments, the present invention provides expression vectors comprising the above polynucleotides, together with host cells transformed with such vectors.

As detailed below, the isolated polynucleotides and polypeptides of the present invention may be usefully employed in the preparation of therapeutic agents for the treatment of immunological disorders.

In related embodiments, methods for modulating the growth of blood vessels, and for the treatment of disorders such as inflammatory disorders, disorders of the immune system, cancer, tumour-necrosis factor-mediated disorders, and viral disorders are provided. Examples of such disorders include HIV-infection; epithelial, lymphoid, myeloid, stromal and neuronal cancers; arthritis; inflammatory bowel disease; and cardiac failure.

The above-mentioned and additional features of the present invention, together with the manner of obtaining them, will be best understood by reference to the following more detailed description. All references disclosed herein are hereby incorporated by reference in their entirety as if each was incorporated individually.

DETAILED DESCRIPTION OF THE INVENTION

In one aspect, the present invention provides polynucleotides isolated from lymph node stromal cells of fsn -/- mice and isolated polypeptides encoded by such polynucleotides.

The term "polynucleotide(s)," as used herein, means a single or double-stranded polymer of deoxyribonucleotide or ribonucleotide bases and includes DNA and corresponding RNA molecules, including HnRNA and mRNA molecules, both sense and anti-sense strands, and comprehends cDNA, genomic DNA and recombinant DNA, as well as wholly or partially synthesized polynucleotides. An HnRNA molecule contains introns and corresponds to a DNA molecule in a generally one-to-one manner. An mRNA molecule corresponds to an HnRNA and DNA molecule from which the introns have been excised. A polynucleotide may consist of an entire gene, or any portion thereof. Operable anti-sense polynucleotides may comprise a fragment of the corresponding polynucleotide, and the definition of "polynucleotide" therefore includes all such operable anti-sense fragments. Anti-sense polynucleotides and techniques involving anti-sense polynucleotides are well known in the art and are described, for example, in Robinson-Benion et al., *Methods in Enzymol.* 254: 363–375, 1995 and Kawasaki et al., *Artific. Organs* 20: 836–848, 1996.

In specific embodiments, the isolated polynucleotides of the present invention comprise a DNA sequence selected from the group consisting of sequences provided in SEQ ID NO: 1–10 and 21–29.

Complements of such isolated polynucleotides, reverse complements of such isolated polynucleotides and reverse sequences of such isolated polynucleotides are also provided, together with polynucleotides comprising at least a specified number of contiguous residues (x-mers) of any of the above-mentioned polynucleotides, extended sequences corresponding to any of the above polynucleotides, anti-sense sequences corresponding to any of the above polynucleotides, and variants of any of the above polynucleotides, as that term is described in this specification.

The definition of the terms "complement", "reverse complement" and "reverse sequence", as used herein, is best illustrated by the following example. For the sequence 5' AGGACC 3', the complement, reverse complement and reverse sequence are as follows:

complement 3' TCCTGG 5'
reverse complement 3' GGTCCT 5'
reverse sequence 5' CCAGGA 3'.

Some of the polynucleotides of the present invention are "partial" sequences, in that they do not represent a full length gene encoding a full length polypeptide. Such partial sequences may be extended by analyzing and sequencing various DNA libraries using primers and/or probes and well known hybridization and/or PCR techniques. Partial sequences may be extended until an open reading frame encoding a polypeptide, a full length polynucleotide and/or gene capable of expressing a polypeptide, or another useful portion of the genome is identified. Such extended sequences, including full length polynucleotides and genes, are described as "corresponding to" a sequence identified as one of the sequences of SEQ ID NO: 1–10 and 21–29, or a variant thereof, or a portion of one of the sequences of SEQ ID NO: 1–10 and 21–29, or a variant thereof, when the extended polynucleotide comprises an identified sequence or its variant, or an identified contiguous portion (x-mer) of one of the sequences of SEQ ID NO: 1–10 and 21–29, or a variant thereof. Such extended polynucleotides may have a length of from about 50 to about 4,000 nucleic acids or base pairs, and preferably have a length of less than about 4,000 nucleic acids or base pairs, more preferably yet a length of less than about 3,000 nucleic acids or base pairs, more preferably yet a length of less than about 2,000 nucleic acids or base pairs. Under some circumstances, extended polynucleotides of the present invention may have a length of less than about 1,800 nucleic acids or base pairs, preferably less than about 1,600 nucleic acids or base pairs, more preferably less than about 1,400 nucleic acids or base pairs, more preferably yet less than about 1,200 nucleic acids or base pairs, and most preferably less than about 1,000 nucleic acids or base pairs.

Similarly, RNA sequences, reverse sequences, complementary sequences, antisense sequences, and the like, corresponding to the polynucleotides of the present invention, may be routinely ascertained and obtained using the cDNA sequences identified as SEQ ID NO: 1–10 and 21–29.

The polynucleotides identified as SEQ ID NO: 1–10 and 21–29 may contain open reading frames ("ORFs") or partial open reading frames encoding polypeptides. Open reading frames may be identified using techniques that are well known in the art. These techniques include, for example, analysis for the location of known start and stop codons, most likely reading frame identification based on codon frequencies, etc. Suitable tools and software for ORF analysis are available, for example, on the Internet at http://www.ncbi.nlm.nih.gov/gorf/gorf.html. Open reading frames and portions of open reading frames may be identified in the polynucleotides of the present invention. Once a partial open reading frame is identified, the polynucleotide may be extended in the area of the partial open reading frame using techniques that are well known in the art until the polynucleotide for the full open reading frame is identified. Thus, open reading frames encoding polypeptides may be identified using the polynucleotides of the present invention.

Once open reading frames are identified in the polynucleotides of the present invention, the open reading frames may be isolated and/or synthesized. Expressible genetic constructs comprising the open reading frames and suitable promoters, initiators, terminators, etc., which are well known in the art, may then be constructed. Such genetic constructs may be introduced into a host cell to express the polypeptide encoded by the open reading frame. Suitable host cells may include various prokaryotic and eukaryotic cells, including plant cells, mammalian cells, bacterial cells, algae and the like.

In another aspect, the present invention provides isolated polypeptides encoded, or partially encoded, by the above polynucleotides. The term "polypeptide", as used herein, encompasses amino acid chains of any length including full length proteins, wherein amino acid residues are linked by covalent peptide bonds. Polypeptides of the present invention may be naturally purified products, or may be produced partially or wholly using recombinant techniques. The term "polypeptide encoded by a polynucleotide" as used herein, includes polypeptides encoded by a nucleotide sequence which includes the partial isolated DNA sequences of the present invention. In specific embodiments, the inventive polypeptides comprise an amino acid sequence selected from the group consisting of sequences provided in SEQ ID NO: 11–20 and 30–38 and variants of such sequences.

Polypeptides encoded by the polynucleotides of the present invention may be expressed and used in various assays to determine their biological activity. Such polypeptides may be used to raise antibodies, to isolate corresponding interacting proteins or other compounds, and to quantitatively determine levels of interacting proteins or other compounds.

All of the polynucleotides and polypeptides described herein are isolated and purified, as those terms are commonly used in the art. Preferably, the polypeptides and polynucleotides are at least about 80% pure, more preferably at least about 90% pure, and most preferably at least about 99% pure.

As used herein, the term "variant" comprehends nucleotide or amino acid sequences different from the specifically identified sequences, wherein one or more nucleotides or amino acid residues is deleted, substituted, or added. Variants may be naturally occurring allelic variants, or non-naturally occurring variants. Variant sequences (polynucleotide or polypeptide) preferably exhibit at least 50%, more preferably at least 75%, and most preferably at least 90% identity to a sequence of the present invention. The percentage identity is determined by aligning the two sequences to be compared, determining the number of identical residues in the aligned portion, dividing that number by the total length of the inventive, or queried, sequence and multiplying the result by 100.

Polynucleotide or polypeptide sequences may be aligned, and percentage of identical residues in a specified region may be determined against another polynucleotide, using computer algorithms that are publicly available. Two exemplary algorithms for aligning and identifying the similarity of polynucleotide sequences are the BLASTN and FASTA algorithms. Polynucleotides may also be analyzed using the BLASTX algorithm, which compares the six-frame conceptual translation products of a nucleotide query sequence (both strands) against a protein sequence database. The similarity of polypeptide sequences may be examined using the BLASTP or FASTX algorithms. Both the BLASTN and BLASTP software are available on the NCBI anonymous FTP server (ftp://ncbi.nlm.nih.gov) under /blast/executables/. The BLASTN algorithm version 2.0.6 [Sep. 16, 1998], set to the default parameters described in the documentation and distributed with the algorithm, is preferred for use in the determination of variants according to the present invention. The use of the BLAST family of algorithms, including BLASTN and BLASTP, is described at NCBI's website at URL http://www.ncbi.nlm.nih.gov/BLAST/newblast.html and in the publication of Altschul et al., "Gapped BLAST and PSI-BLAST: a new generation of protein database search programs", *Nucleic Acids Res.* 25:3389–3402, 1997. The computer algorithm FASTA is available on the Internet at the ftp site fti://ftp.virginia.edu/pub/fasta/. Version3.1t11, August 1998, set to the default parameters described in the documentation and distributed with the algorithm, is preferred for use in the determination of variants according to the present invention. The use of the FASTA algorithm is described in Pearson and Lipman, "Improved Tools for Biological Sequence Analysis," *Proc. Natl. Acad. Sci. USA* 85:2444–2448, 1988 and Pearson, "Rapid and Sensitive Sequence Comparison with FASTP and FASTA," *Methods in Enzymology* 183:63–98, 1990. The use of the FASTX algorithm is described in Pearson et al., "Comparison of DNA sequences with protein sequences," *Genomics* 46:24–36, 1997.

The following running parameters are preferred for determination of alignments and similarities using BLASTN that contribute to the E values and percentage identity: Unix running command: blastall -p blastn -d embldb -e 10-G 0-E 0-r 1-v 30-b 30-i queryseq - results; and parameter default values:
-p Program Name [String]
-d Database [String]
-e Expectation value (E) [Real]
-G Cost to open a gap (zero invokes default behavior) [Integer]
-E Cost to extend a gap (zero invokes default behavior) [Integer]
-r Reward for a nucleotide match (blastn only) [Integer]
-v Number of one-line descriptions (V) [Integer]

-b Number of alignments to show (B) [Integer]
-i Query File [File In]
-o BLAST report Output File [File Out] Optional
For BLASTP the following running parameters are preferred: blastall -p blastp -d swissprotdb -e 10-G 0-E 0-v 30-b 30-i queryseq o results
-p Program Name [String]
-d Database [String]
-e Expectation value (E) [Real]
-G Cost to open a gap (zero invokes default behavior) [Integer]
-E Cost to extend a gap (zero invokes default behavior) [Integer]
-v Number of one-line descriptions (v) [Integer]
-b Number of alignments to show (b) [Integer]
-I Query File [File In]
-o BLAST report Output File [File Out] Optional The "hits" to one or more database sequences by a queried sequence produced by BLASTN, BLASTP, FASTA, or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN and FASTA algorithms also produce "Expect" values for alignments. The Expect value (E) indicates the number of hits one can "expect" to see over a certain number of contiguous sequences by chance when searching a database of a certain size. The Expect value is used as a significance threshold for determining whether the hit to a database, such as the preferred EMBL database, indicates true similarity. For example, an E value of 0.1 assigned to a hit is interpreted as meaning that in a database of the size of the EMBL database, one might expect to see 0.1 matches over the aligned portion of the sequence with a similar score simply by chance. By this criterion, the aligned and matched portions of the sequences then have a probability of 90% of being the same. For sequences having an E value of 0.01 or less over aligned and matched portions, the probability of finding a match by chance in the EMBL database is 1% or less using the BLASTN or FASTA algorithm.

According to one embodiment, "variant" polynucleotides, with reference to each of the polynucleotides of the present invention, preferably comprise sequences having the same number or fewer nucleic acids than each of the polynucleotides of the present invention and producing an E value of 0.01 or less when compared to the polynucleotide of the present invention. That is, a variant polynucleotide is any sequence that has at least a 99% probability of being the same as the polynucleotide of the present invention, measured as having an E value of 0.01 or less using the BLASTN or FASTA algorithms set at the default parameters. According to a preferred embodiment, a variant polynucleotide is a sequence having the same number or fewer nucleic acids than a polynucleotide of the present invention that has at least a 99% probability of being the same as the polynucleotide of the present invention, measured as having an E value of 0.01 or less using the BLASTN or FASTA algorithms set at the default parameters.

Alternatively, variant polynucleotide sequences hybridize to the recited polynucleotide sequence under stringent conditions. As used herein, "stringent conditions" refers to prewashing in a solution of 6xSSC, 0.2% SDS; hybridizing at 65° C., 6xSSC, 0.2% SDS overnight; followed by two washes of 30 minutes each in 1xSSC, 0.1% SDS at 65° C. and two washes of 30 minutes each in 0.2xSSC, 0.1% SDS at 65° C.

The present invention also encompasses polynucleotides that differ from the disclosed sequences but that, as a consequence of the degeneracy of the genetic code, encode a polypeptide which is the same as that encoded by a polynucleotide of the present invention. Thus, polynucleotides comprising sequences that differ from the polynucleotide sequences provided in SEQ ID NO: 1–10 and 21–29, or complements, reverse sequences, or reverse complements thereof, as a result of conservative substitutions are contemplated by and encompassed within the present invention. Additionally, polynucleotides comprising sequences that differ from the polynucleotide sequences provided in SEQ ID NO: 1–10 and 21–29, or complements, reverse complements or reverse sequences thereof, as a result of deletions and/or insertions totaling less than 10% of the total sequence length are also contemplated by and encompassed within the present invention. Similarly, polypeptides comprising sequences that differ from the polypeptide sequences provided in SEQ ID NO: 11–20 and 30–38, as a result of amino acid substitutions, insertions, and/or deletions totaling less than 10% of the total sequence length are contemplated by and encompassed within the present invention.

Polynucleotides of the present invention also comprehend polynucleotides comprising at least a specified number of contiguous residues (x-mers) of any of the polynucleotides identified as SEQ ID NO: 1–10 and 21–29, complements, reverse sequences, and reverse complements of such sequences, and their variants. Similarly, polypeptides of the present invention comprehend polypeptides comprising at least a specified number of contiguous residues (x-mers) of any of the polypeptides identified as SEQ ID NO: 11–20 and 30–38, and their variants. As used herein, the term "x-mer," with reference to a specific value of "x," refers to a sequence comprising at least a specified number ("x") of contiguous residues of any of the polynucleotides identified as SEQ ID NO: 1–10 and 21–29, or the polypeptides identified as SEQ ID NO: 11–20 and 30–38. According to preferred embodiments, the value of x is preferably at least 20, more preferably at least 40, more preferably yet at least 60, and most preferably at least 80. Thus, polynucleotides and polypeptides of the present invention comprise a 20-mer, a 40-mer, a 60-mer, an 80-mer, a 100-mer, a 120-mer, a 150-mer, a 180-mer, a 220-mer, a 250-mer, a 300-mer, 400-mer, 500-mer or 600-mer of a polynucleotide or polypeptide identified as SEQ ID NO: 1–38, and variants thereof.

The inventive polynucleotides may be isolated by high throughput sequencing of cDNA libraries prepared from lymph node stromal cells of fsn -/- mice as described below in Example 1. Alternatively, oligonucleotide probes based on the sequences provided in SEQ ID NO: 1–10 and 21–29 can be synthesized and used to identify positive clones in either cDNA or genomic DNA libraries from lymph node stromal cells of fsn -/- mice by means of hybridization or polymerase chain reaction (PCR) techniques. Probes can be shorter than the sequences provided herein but should be at least about 10, preferably at least about 15 and most preferably at least about 20 nucleotides in length. Hybridization and PCR techniques suitable for use with such oligonucleotide probes are well known in the art (see, for example, Mullis et al., *Cold Spring Harbor Symp. Quant. Biol.*, 51:263, 1987; Erlich ed., *PCR Technology*, Stockton Press, NY, 1989; Sambrook et al., *Molecular cloning—a laboratory manual*, Cold Spring Harbor Laboratory Press, Cold Spring Harbor, N.Y., 1989). Positive clones may be analyzed by restriction enzyme digestion, DNA sequencing or the like.

The polynucleotides of the present invention may alternatively be synthesized using techniques that are well known in the art. The polynucleotides may be synthesized, for example, using automated oligonucleotide synthesizers (e.g., Beckman Oligo 1000M DNA Synthesizer) to obtain polynucleotide segments of up to 50 or more nucleic acids. A plurality of such polynucleotide segments may then be ligated using standard DNA manipulation techniques that are well known in the art of molecular biology. One conventional and exemplary polynucleotide synthesis technique involves synthesis of a single stranded polynucleotide segment having, for example, 80 nucleic acids, and hybridizing that segment to a synthesized complementary 85 nucleic acid segment to produce a 5 nucleotide overhang. The next segment may then be synthesized in a similar fashion, with a 5 nucleotide overhang on the opposite strand. The "sticky" ends ensure proper ligation when the two portions are hybridized. In this way, a complete polynucleotide of the present invention may be synthesized entirely in vitro.

Polypeptides of the present invention may be produced recombinantly by inserting a DNA sequence that encodes the polypeptide into an expression vector and expressing the polypeptide in an appropriate host. Any of a variety of expression vectors known to those of ordinary skill in the art may be employed. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are E. coli, insect, yeast or a mammalian cell line such as COS or CHO. The DNA sequences expressed in this manner may encode naturally occurring polypeptides, portions of naturally occurring polypeptides, or other variants thereof.

In a related aspect, polypeptides are provided that comprise at least a functional portion of a polypeptide having an amino acid sequence selected from the group consisting of sequences provided in SEQ ID NO: 11–20 and 30–38 and variants thereof. As used herein, the "functional portion" of a polypeptide is that portion which contains the active site essential for affecting the function of the polypeptide, for example, the portion of the molecule that is capable of binding one or more reactants. The active site may be made up of separate portions present on one or more polypeptide chains and will generally exhibit high binding affinity. Such functional portions generally comprise at least about 5 amino acid residues, more preferably at least about 10, and most preferably at least about 20 amino acid residues. Functional portions of the inventive polypeptides may be identified by first preparing fragments of the polypeptide, by either chemical or enzymatic digestion of the polypeptide or mutation analysis of the polynucleotide that encodes for the polypeptide, and subsequently expressing the resultant mutant polypeptides. The polypeptide fragments or mutant polypeptides are then tested to determine which portions retain the biological activity of the full-length polypeptide.

Portions and other variants of the inventive polypeptides may be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain (Merrifield, *J. Am. Chem. Soc.* 85:2149–2154, 1963). Equipment for automated synthesis of polypeptides is commercially available from suppliers such as Perkin Elmer/Applied BioSystems, Inc. (Foster City, Calif.), and may be operated according to the manufacturer's instructions. Variants of a native polypeptide may be prepared using standard mutagenesis techniques, such as oligonucleotide-directed site-specific mutagenesis (see, for example, Kunkel, *Proc. Natl. Acad. Sci. USA* 82:488–492, 1985). Sections of DNA sequence may also be removed using standard techniques to permit preparation of truncated polypeptides.

Since the polynucleotide sequences of the present invention have been derived from fsn -/- mouse lymph node stromal cells, they likely encode proteins that have important role(s) in growth and development of the immune system, and in responses of the immune system to tissue injury and inflammation as well as other disease states. Some of the polynucleotides contain sequences that code for signal sequences, or transmembrane domains, which identify the protein products as secreted molecules or receptors. Such protein products are likely to be growth factors, cytokines, or their cognate receptors. The polypeptide sequence of SEQ ID NO: 13 has more than 25% identity to known members of the tumour necrosis factor (TNF) receptor family of proteins, with the polypeptides of SEQ ID NO: 30, 31, 32 and 33 having more than 25% identity to known members of the fibroblast growth factor (FGF) receptor family of proteins, and the polypeptide of SEQ ID NO: 38 having more than 25% identity to known members of the WDNM1 family of proteins. These inventive polypeptides are thus likely to have similar biological functions.

In particular, the inventive polypeptides may have important roles in processes such as: modulation of immune responses; differentiation of precursor immune cells into specialized cell types; cell migration; cell proliferation and cell-cell interaction. The polypeptides may be important in the defence of the body against infectious agents, and thus be of importance in maintaining a disease-free environment. These polypeptides may act as modulators of skin cells, especially since immune cells are known to infiltrate skin during tissue insult, causing growth and differentiation of skin cells. In addition, these proteins may be immunologically active, making them important therapeutic targets in a large range of disease states.

In one aspect, the present invention provides methods for using one or more of the inventive polypeptides or polynucleotides to treat disorders in a patient. As used herein, a "patient" refers to any warm-blooded animal, preferably a human.

In this aspect, the polypeptide or polynucleotide is generally present within a pharmaceutical composition or a vaccine. Pharmaceutical compositions may comprise-one or more polypeptides, each of which may contain one or more of the above sequences (or variants thereof), and a physiologically acceptable carrier. Vaccines may comprise one or more of the above polypeptides and a non-specific immune response amplifier, such as an adjuvant or a liposome, into which the polypeptide is incorporated.

Alternatively, a vaccine or pharmaceutical composition of the present invention may contain DNA encoding one or more polypeptides as described above, such that the polypeptide is generated in situ. In such vaccines and pharmaceutical compositions, the DNA may be present within any of a variety of delivery systems known to those of ordinary skill in the art, including nucleic acid expression systems, and bacterial and viral expression systems. Appropriate nucleic acid expression systems contain the necessary DNA sequences for expression in the patient (such as a suitable promoter and terminator signal). Bacterial delivery systems involve the administration of a bacterium (such as Bacillus Calmette-Guerin) that expresses an immunogenic portion of the polypeptide on its cell surface. In a preferred embodiment, the DNA may be introduced using a viral expression system (e.g., vaccinia or other poxvirus, retrovirus, or adenovirus), which may involve the use of a non-pathogenic, or defective, replication competent virus. Techniques for incorporating DNA into such expression systems are well known in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

Routes and frequency of administration, as well as dosage, will vary from individual to individual. In general, the pharmaceutical compositions and vaccines may be administered by injection (e.g., intradermal, intramuscular, intravenous or subcutaneous), intranasally (e.g., by aspiration) or orally. In general, the amount of polypeptide present in a dose (or produced in situ by the DNA in a dose) ranges from about 1 pg to about 100 mg per kg of host, typically from about 10 pg to about 1 mg per kg of host, and preferably from about 100 pg to about 1 μg per kg of host. Suitable dose sizes will vary with the size of the patient, but will typically range from about 0.1 ml to about 5 ml.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a lipid, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

Any of a variety of adjuvants may be employed in the vaccines derived from this invention to non-specifically enhance the immune response. Most adjuvants contain a substance designed to protect the antigen from rapid catabolism, such as aluminum hydroxide or mineral oil, and a non-specific stimulator of immune responses, such as lipid A, *Bordetella pertussis* or *M. tuberculosis*. Suitable adjuvants are commercially available as, for example, Freund's Incomplete Adjuvant and Freund's Complete Adjuvant (Difco Laboratories, Detroit, Mich.), and Merck Adjuvant 65 (Merck and Company, Inc., Rahway, N.J.). Other suitable adjuvants include alum, biodegradable microspheres, monophosphoryl lipid A and Quil A.

The polynucleotides of the present invention may also be used as markers for tissue, as chromosome markers or tags, in the identification of genetic disorders, and for the design of oligonucleotides for examination of expression patterns using techniques well known in the art, such as the microarray technology available from Synteni (Palo Alto, Calif.). Partial polynucleotide sequences disclosed herein may be employed to obtain full length genes by, for example, screening of DNA expression libraries, and to isolate homologous DNA sequences from other species using hybridization probes or PCR primers based on the inventive sequences.

The isolated polynucleotides of the present invention also have utility in genome mapping, in physical mapping, and in positional cloning of genes. As detailed below, the polynucleotide sequences identified as SEQ ID NO: 1–10 and 21–29, and their variants, may be used to design oligonucleotide probes and primers. Oligonucleotide probes designed using the polynucleotides of the present invention may be used to detect the presence and examine the expression patterns of genes in any organism having sufficiently similar DNA and RNA sequences in their cells using techniques that are well known in the art, such as slot blot DNA hybridization techniques. Oligonucleotide primers designed using the polynucleotides of the present invention may be used for PCR amplifications. Oligonucleotide probes and primers designed using the polynucleotides of the present invention may also be used in connection with various microarray technologies, including the microarray technology of Synteni (Palo Alto, Calif.).

As used herein, the term "oligonucleotide" refers to a relatively short segment of a polynucleotide sequence, generally comprising between 6 and 60 nucleotides, and comprehends both probes for use in hybridization assays and primers for use in the amplification of DNA by polymerase chain reaction. An oligonucleotide probe or primer is described as "corresponding to" a polynucleotide of the present invention, including one of the sequences set out as SEQ ID NO: 1–10 and 21–29, or a variant thereof, if the oligonucleotide probe or primer, or its complement, is contained within one of the sequences set out as SEQ ID NO: 1–10 and 21–29, or a variant of one of the specified sequences. Oligonucleotide probes and primers of the present invention are substantially complementary to a polynucleotide disclosed herein.

Two single stranded sequences are said to be substantially complementary when the nucleotides of one strand, optimally aligned and compared, with the appropriate nucleotide insertions and/or deletions, pair with at least 80%, preferably at least 90% to 95% and more preferably at least 98% to 100% of the nucleotides of the other strand. Alternatively, substantial complementarity exists when a first DNA strand will selectively hybridize to a second DNA strand under stringent hybridization conditions. Stringent hybridization conditions for determining complementarity include salt conditions of less than about 1 M, more usually less than about 500 mM, and preferably less than about 200 mM. Hybridization temperatures can be as low as 5° C., but are generally greater than about 22° C., more preferably greater than about 30° C., and most preferably greater than about 37° C. Longer DNA fragments may require higher hybridization temperatures for specific hybridization. Since the stringency of hybridization may be affected by other factors such as probe composition, presence of organic solvents and extent of base mismatching, the combination of parameters is more important than the absolute measure of any one alone.

In specific embodiments, the oligonucleotide probes and/or primers comprise at least about 6 contiguous residues, more preferably at least about 10 contiguous residues, and most preferably at least about 20 contiguous residues complementary to a polynucleotide sequence of the present invention. Probes and primers of the present invention may be from about 8 to 100 base pairs in length or, preferably from about 10 to 50 base pairs in length or, more preferably from about 15 to 40 base pairs in length. The probes can be easily selected using procedures well known in the art, taking into account DNA-DNA hybridization stringencies, annealing and melting temperatures, and potential for formation of loops and other factors, which are well known in the art. Tools and software suitable for designing probes, and especially suitable for designing PCR primers, are available on the Internet, for example, at URL http://www.horizonpress.com/per/. Preferred techniques for designing PCR primers are also disclosed in Dieffenbach, C W and Dyksler, G S. *PCR Primer: a laboratory manual*, CSHL Press: Cold Spring Harbor, N.Y., 1995.

A plurality of oligonucleotide probes or primers corresponding to a polynucleotide of the present invention may be provided in a kit form. Such kits generally comprise multiple DNA or oligonucleotide probes, each probe being specific for a polynucleotide sequence. Kits of the present invention may comprise one or more probes or primers corresponding to a polynucleotide of the present invention, including a polynucleotide sequence identified in SEQ ID NO: 1–10 and 21–29.

In one embodiment useful for high-throughput assays, the oligonucleotide probe kits of the present invention comprise multiple probes in an array format, wherein each probe is immobilized at a predefined, spatially addressable location on the surface of a solid substrate. Array formats which may be usefully employed in the present invention are disclosed, for example, in U.S. Pat. Nos. 5,412,087 and 5,545,451, and PCT Publication No. WO 95/00450, the disclosures of which are hereby incorporated by reference.

The polynucleotides of the present invention may also be used to tag or identify an organism or reproductive material therefrom. Such tagging may be accomplished, for example, by stably introducing a non-disruptive non-functional heterologous polynucleotide identifier into an organism, the polynucleotide comprising one of the polynucleotides of the present invention.

The polypeptides provided by the present invention may additionally be used in assays to determine biological activity, to raise antibodies, to isolate corresponding ligands or receptors, in assays to quantify levels of protein or cognate corresponding ligand or receptor, as antiinflammatory agents, and in compositions for the treatment of diseases of skin, connective tissue and the immune system.

EXAMPLE 1

Isolation of cDNA Sequences from Lymph Node Stromal Cell Expression Libraries

The cDNA sequences of the present invention were obtained by high-throughput sequencing of cDNA expression libraries constructed from rodent fsn -/- lymph node stromal cells as described below.

cDNA Libraries from Lymph Node Stromal Cells (MLSA and MLSE)

Lymph nodes were removed from flaky skin fsn -/- mice, the cells dissociated and the resulting single cell suspension placed in culture. After four passages, the cells were harvested. Total RNA, isolated using TRIzol Reagent (BRL Life Technologies, Gaithersburg, Md.), was used to obtain MRNA using a Poly(A) Quik mRNA isolation kit (Stratagene, La Jolla, Calif.), according to the manufacturer's specifications. A cDNA expression library (referred to as the MLSA library) was then prepared from the mRNA by Reverse Transcriptase synthesis using a Lambda ZAP Express cDNA library synthesis kit (Stratagene, La Jolla, Calif.). A second cDNA expression library, referred to as the MLSE library, was prepared exactly as above except that the cDNA was inserted into the mammalian expression vector pcDNA3 (Invitrogen, Carlsbad Calif.).

The nucleotide sequence of the cDNA clone isolated from the MLSE library is given in SEQ ID NO: 1, with the corresponding amino acid sequence being provided in SEQ ID NO: 11. The nucleotide sequences of the cDNA clones isolated from the MLSA library are given in SEQ ID NO: 2–10, 21–23 and 28, with the corresponding amino acid sequences being provided in SEQ ID NO: 12–20, 30–32 and 37, respectively.

Subtracted cDNA Library from Flaky Skin Lymph Node Stromal Cells (MLSS)

Stromal cells from flaky skin mice lymph nodes and 3T3 fibroblasts were grown in culture and the total RNA extracted from these cells using established protocols. Total RNA from both populations was isolated using TRIzol Reagent (Gibco BRL Life Technologies, Gaitherburg, Md.) and used to obtain mRNA using either a Poly (A) Quik mRNA isolation kit (Stratagene, La Jolla, Calif.) or Quick Prep(R) Micro mRNA purification kit (Pharmacia, Uppsala, Sweden). Double-stranded cDNA from flaky skin lymph node stromal cell mRNA was prepared by Reverse Transcriptase synthesis using a lambda ZAP cDNA library synthesis kit (Stratagene) that had been ligated with EcoRI adaptors and digested with XhoI to produce double-stranded fragments with EcoRI and XhoI overhanging ends.

Double-stranded cDNA from 3T3 fibroblasts was prepared using the Superscript II reverse transcriptase (Gibco BRL Life Technologies) followed by treatment with DNA polymerase I and RNaseH (Gibco BRL Life Technologies). Double-stranded 3T3 cDNA was then digested with restriction endonucleases AluI and RsaI (Gibco BRL Life Technologies) to produce blunt-ended fragments. A 20-fold excess of AluI/RsaI-digested 3T3 cDNA was hybridized with the EcoRI/XhoI flaky skin lymph node stromal cell cDNA in the following hybridisation solution: 50% formamide, 5×SSC, 10 mM $NaH_2PO_4$ pH7.5, 1 mM EDTA, 0.1% SDS, 200 µg yeast tRNA (Boehringer Mannheim) at 37° C. for 24 hours. Hybridized flaky skin lymph node stromal cell cDNA and 3T3 cDNA was then phenol/chloroform extracted and ethanol precipitated. The cDNA was size-fractionated over a Sepharose CL-2B gel filtration column as described in the Lambda ZAP cDNA library synthesis protocol (Stratagene). Flaky skin lymph node stromal cell-specific cDNA was preferentially ligated into ZAP Express vector (Stratagene) by virtue of EcoRI/XhoI ends. Chimeric cDNA between flaky skin lymph node stromal cell cDNA and 3T3 cDNA would not be cloned due to non-compatible ends, and the subtracted cDNA library was packaged using Gigapack III Gold packaging extract (Stratagene).

The nucleotide sequences of the cDNA clones isolated from the MLSS library are given in SEQ ID NO: 25–27 and 29, with the corresponding amino acid sequences being provided in SEQ ID NO: 34–36 and 38, respectively.

EXAMPLE 2

Characterization of Isolated cDNA Sequences

The isolated cDNA sequences were compared to sequences in the EMBL DNA database using the computer algorithm BLASTN, and the corresponding predicted protein sequences (DNA translated to protein in each of 6 reading frames) were compared to sequences in the SwissProt database using the computer algorithm BLASTP. Specifically, comparisons of DNA sequences provided in SEQ ID NO: 1–10 and 21–29 to sequences in the EMBL (Release 58, March 1999) DNA database, and amino acid sequences provided in SEQ ID NO: 11–20 and 30–38 to sequences in the SwissProt and TrEMBL (up to Jun. 8, 1999) databases were made as of Jul. 29, 1999. The cDNA sequences of SEQ ID NO: 1–10, 21–24 and 27–28, and their corresponding predicted amino acid sequences (SEQ ID NO: 11–20, 30–33 and 36–37, respectively) were determined to have less than 75% identity (determined as described above) to sequences in the EMBL and SwissProt databases using the computer algorithms BLASTN and BLASTP, respectively.

Isolated cDNA sequences and their corresponding predicted protein sequences, were computer analyzed for the presence of signal sequences identifying secreted molecules. Isolated cDNA sequences that have a signal sequence at a putative start site within the sequence are provided in SEQ ID NO: 4–6, 9–10 and 25–26. The isolated cDNA sequences were also computer analyzed for the presence of transmembrane domains coding for putative membrane-bound molecules. Isolated cDNA sequences that have one or more transmembrane domain(s) within the sequence are provided in SEQ ID NO: 1–3, 7, 8 and 27.

Using automated search programs to screen against sequences coding for known molecules reported to be of therapeutic and/or diagnostic use, the isolated cDNA sequence of SEQ ID NO: 3, 21–24 and 29 were determined to encode predicted protein sequences that appear to be members of the tumour necrosis factor (TNF) receptor family of proteins (SEQ ID NO: 13), the fibroblast growth factor (FGF) receptor family (SEQ ID NO: 30–33) and the WDNM1 protein family (SEQ ID NO: 38). A family member is here defined to have at least 20% identical amino acid residues in the translated polypeptide to a known protein or member of a protein family.

As noted above, the isolated cDNA sequence of SEQ ID NO: 3 was determined to encode a predicted protein sequence (SEQ ID NO: 13) that appears to be a member of the TNF-receptor family. Proteins of the TNF/NGF-receptor family are involved in the proliferation, differentiation and death of many cell types including B and T lymphocytes. Residues 18–55 of SEQ ID NO: 13 show a high degree of similarity to the Prosite motif for the TNF/NGF receptor family (Banner et al., *Cell* 73:431–445, 1993). This motif contributes to the ligand binding domain of the molecule and is thus essential to its function. (Gruss and Dower, *Blood* 85:3378–3404, 1995). The polypeptide of SEQ ID NO: 13 is therefore likely to influence the growth, differentiation and activation of several cell types, and may be usefully developed as an agent for the treatment of skin wounds, and the treatment and diagnosis of cancers, inflammatory diseases, and growth and developmental defects.

The isolated cDNA sequence of SEQ ID NO: 29 was determined to encode a predicted protein sequence (SEQ ID NO: 38) that appears to be a member of the WDNM1 protein family. The WDNM1 family of proteins has a conserved arrangement of cysteine residues. The family includes several proteinase inhibitors, suggesting that WDNM1 could encode a product with proteinase inhibiting capacity. The WDNM1 gene has been shown to be down-regulated in metastatic rat mammary adenocarcinomas (Dear and Kefford, *Biochem. Biophys. Res. Commun.* 176:247–254, 1991).

The isolated cDNA sequence of SEQ ID NO: 21 was determined to encode a predicted protein sequence (SEQ ID NO: 30) that appears to be a member of the fibroblast growth factor (FGF) receptor family of proteins, specifically the FGF receptor 3. Fibroblast growth factor receptors belong to a family of four single membrane-spanning tyrosine kinases (FGFR1 to 4). These receptors serve as high-affinity receptors for 17 growth factors (FGF1 to 17). FGF receptors have important roles in multiple biological processes, including mesoderm induction and patterning, cell growth and migration, organ formation and bone growth (Xu, *Cell Tissue Res.* 296:33–43, 1999). Further analysis of the sequence revealed the presence of a putative transmembrane domain and intracellular domain, similar to other FGF receptors.

EXAMPLE 3

Isolation of Full Length cDNA Sequence of a Murine Fibroblast Growth Factor Receptor Homologue The full-length cDNA sequence of a murine fibroblast growth factor receptor homologue was isolated as follows.

The MLSA cell cDNA library (described in Example 1) was screened with an [$\alpha^{32}$P]-dCTP labeled cDNA probe corresponding to nucleotides 1 to 451 of the coding region within SEQ ID NO: 21. Plaque lifts, hybridization and screening were performed using standard molecular biology techniques. The determined polynucleotide sequence of the full-length murine FGFR gene (referred to as muFGFR-β) is provided in SEQ ID NO: 22, with the corresponding predicted amino acid sequence being provided in SEQ ID NO: 31.

Analysis of the polynucleotide sequence of SEQ ID NO: 22 revealed the presence of a putative transmembrane domain corresponding to nucleotides 1311 to 1370. The polypeptide sequence (SEQ ID NO: 31) has regions similar to the extracellular domain of the fibroblast growth factor receptor family.

A splice variant of SEQ ID: 22 was also isolated from the MLSA cDNA library as described in Example 1. The determined polynucleotide sequence of the splice variant (referred to as FGFR-γ) is provided in SEQ ID NO: 23 and the corresponding predicted amino acid sequence is provided in SEQ ID NO: 32. The splice regions are in an equivalent position to splice sites for previously described FGF receptors (Ornitz, *J. Biol. Chem.* 296:15292–15297, 1996; Wilkie, *Current Biology* 5:500–507, 1995; Miki, *Proc. Natl. Acad. Sci. USA* 89:246–250, 1992), thus providing further evidence that this molecule is a FGF receptor homologue.

EXAMPLE 4

Isolation of a Human FGF Receptor Homologue

The cDNA EST encoding the partial murine FGF receptor (SEQ ID NO: 21) was used to search the EMBL database (Release 58, March 1999) to identify human EST homologues. The identified EST (Accession Number AI245701) was obtained from Research Genetics, Inc (Huntsville Ala.) as I.M.A.G.E. Consortium clone ID 1870593. Sequence determination of the complete insert of clone 1870593 resulted in the identification of 520 additional nucleotides. The insert of this clone did not represent the full-length gene. The determined nucleotide sequence of the complete insert of clone 1870593 is given in SEQ ID NO: 24 and the corresponding predicted amino acid sequence in SEQ ID NO: 33.

What is claimed is:

1. An isolated polypeptide comprising SEQ ID NO: 31.
2. An isolated polypeptide comprising SEQ ID NO: 32.
3. An isolated polypeptide comprising SEQ ID NO: 33.
4. An isolated polypeptide comprising a sequence selected from the group consisting of sequences having at least 90% identity to SEQ ID NO: 31 as determined using the computer algorithm BLASTP, wherein the polypeptide is able to bind to fibroblast growth factor.
5. An isolated polypeptide comprising a sequence selected from the group consisting of sequences having at least 90% identity to SEQ ID NO: 32 as determined using the computer algorithm BLASTP, wherein the polypeptide is able to bind to fibroblast growth factor.
6. An isolated polypeptide comprising a sequence selected from the group consisting of sequences having at least 90% identity to SEQ ID NO: 33 as determined using the computer algorithm BLASTP, wherein the polypeptide is able to bind to fibroblast growth factor.
7. A pharmaceutical composition comprising an isolated polypeptide according to any one of claims 1–6.

* * * * *

UNITED STATES PATENT AND TRADEMARK OFFICE
CERTIFICATE OF CORRECTION

PATENT NO. : 6,242,419 B1  
DATED : June 5, 2001  
INVENTOR(S) : Matthew Sleeman Page 1 of 1

It is certified that error appears in the above-identified patent and that said Letters Patent is hereby corrected as shown below:

<u>Title page,</u>  
Item [75], delete Inventors Lorna Strachan, Nevin Abernethy, Rene Onrust, Anand Kumble and Greg Murison, leaving Matthew Sleeman as the sole inventor.

Signed and Sealed this

Second Day of April, 2002

*Attest:*

JAMES E. ROGAN  
*Attesting Officer*     *Director of the United States Patent and Trademark Office*